US012729257B2

(12) United States Patent
Huacuja et al.

(10) Patent No.: US 12,729,257 B2
(45) Date of Patent: Sep. 8, 2026

(54) OLEFIN POLYMERIZATION BIMETALLIC ACTIVATORS

(71) Applicant: Dow Global Technologies LLC, Midland, MI (US)

(72) Inventors: Rafael Huacuja, Lake Jackson, TX (US); Richard Keaton, Lake Jackson, TX (US); Jerzy Klosin, Midland, MI (US); Sukrit Mukhopadhyay, Midland, MI (US); David M. Pearson, Lake Jackson, TX (US); Todd D. Senecal, Midland, MI (US); William H.H. Woodward, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 824 days.

(21) Appl. No.: 17/922,923

(22) PCT Filed: May 7, 2021

(86) PCT No.: PCT/US2021/031233

§ 371 (c)(1),
(2) Date: Nov. 2, 2022

(87) PCT Pub. No.: WO2021/226423

PCT Pub. Date: Nov. 11, 2021

(65) Prior Publication Data

US 2023/0174693 A1 Jun. 8, 2023

Related U.S. Application Data

(60) Provisional application No. 63/021,419, filed on May 7, 2020.

(51) Int. Cl.

| | |
|---|---|
| ***C08F 4/52*** | (2006.01) |
| ***C07D 233/54*** | (2006.01) |
| ***C07F 5/02*** | (2006.01) |
| ***C07F 7/08*** | (2006.01) |
| ***C08F 4/64*** | (2006.01) |
| ***C08F 210/16*** | (2006.01) |

(52) U.S. Cl.

CPC ............ *C08F 210/16* (2013.01); *C07F 5/027* (2013.01); *C07F 7/0814* (2013.01); *C08F 4/52* (2013.01); *C07D 233/54* (2013.01); *C08F 4/64* (2013.01)

(58) Field of Classification Search

CPC .................................... C08F 4/52; C08F 4/64
See application file for complete search history.

(56) References Cited

U.S. PATENT DOCUMENTS

| | | | |
|---|---|---|---|
| 3,773,733 A | 11/1973 | Matsushima | |
| 3,860,622 A | 1/1975 | Wade | |
| 4,677,088 A | 6/1987 | Huff et al. | |
| 5,347,024 A | 9/1994 | Nickias et al. | |
| 5,407,882 A | 4/1995 | Yamada et al. | |
| 5,447,895 A | 9/1995 | Marks et al. | |
| 5,536,797 A | 7/1996 | Nickias et al. | |
| 5,763,549 A | 6/1998 | Elder et al. | |
| 5,807,939 A | 9/1998 | Elder et al. | |
| 5,895,771 A | 4/1999 | Epstein et al. | |
| 5,919,983 A | 7/1999 | Rosen et al. | |
| 6,153,776 A | 11/2000 | Patton et al. | |
| 6,177,376 B1 | 1/2001 | Fritze et al. | |
| 6,221,941 B1 | 4/2001 | Strauss et al. | |
| 6,268,445 B1 | 7/2001 | McAdon et al. | |
| 6,284,697 B1 | 9/2001 | Windisch et al. | |
| 6,392,076 B1 | 5/2002 | Strauss et al. | |
| 6,395,671 B2 * | 5/2002 | LaPointe | C08F 10/00 502/103 |
| 6,455,650 B1 | 9/2002 | Lipian et al. | |
| 6,462,156 B2 | 10/2002 | LaPointe | |
| 6,627,573 B2 * | 9/2003 | Babb | C07F 7/0803 502/414 |
| 6,716,786 B1 * | 4/2004 | Campbell, Jr. | C07F 5/027 502/103 |

(Continued)

FOREIGN PATENT DOCUMENTS

| | | |
|---|---|---|
| CA | 2254601 A1 | 11/1998 |
| CN | 1270596 A | 10/2000 |

(Continued)

OTHER PUBLICATIONS

Brazil Office Action dated Aug. 30, 2023, pertaining to BR Patent Application No. BR112020019339-9, 10 pgs.
Japanese Office Action dated Sep. 26, 2023, pertaining to JP Patent Application No. 2020-551475, 6 pgs.
Chinese Office Action dated Sep. 4, 2023, pertaining to Chinese Patent Application No. 201980022602.8, 6 pgs.
European Examination Report dated Sep. 1, 2023, pertaining to European Patent Application No. 19716692.9, 5 pgs.
Chinese Office Action dated Jan. 15, 2024, pertaining to CN Patent Application No. 202180033239.7, 14 pgs.
US Notice of Allowance dated Mar. 6, 2024, pertaining to U.S. Appl. No. 17/043,029, 9 pgs.
Korean Office Action dated Sep. 12, 2024, pertaining to KR Patent Application No. 10-2020-7029426, 6 pgs.

(Continued)

*Primary Examiner* — Rip A Lee
(74) *Attorney, Agent, or Firm* — Dinsmore & Shohl LLP

(57) ABSTRACT

Processes of polymerizing olefins. The process includes polymerizing contacting ethylene and a $(C_3-C_{40})$alpha-olefin comonomer in the presence of a catalyst system comprising a procatalyst and a bimetallic activator complex. The bimetallic activator complex includes an anion and a countercation. The anion having a structure according to formula (I).

(I)

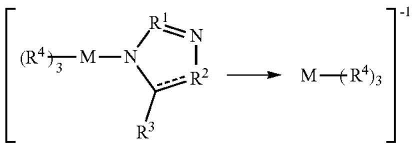

11 Claims, No Drawings

(56) References Cited

U.S. PATENT DOCUMENTS

| | | | |
|---|---|---|---|
| 6,777,509 B2 | 8/2004 | Brown et al. | |
| 6,869,904 B2 | 3/2005 | Boussie et al. | |
| 6,900,321 B2 | 5/2005 | Boussie et al. | |
| 6,953,764 B2 | 10/2005 | Frazier et al. | |
| 7,078,546 B2 | 7/2006 | Piers et al. | |
| 7,196,149 B2 | 3/2007 | Collins et al. | |
| 7,511,104 B2 | 3/2009 | Pehlert et al. | |
| 7,579,416 B2 | 8/2009 | Mihan | |
| 7,619,047 B2 | 11/2009 | Yang et al. | |
| 7,650,930 B2 | 1/2010 | Cheluget et al. | |
| 7,683,194 B2 | 3/2010 | Krossing et al. | |
| 7,951,882 B2 * | 5/2011 | Arriola | C08L 23/0815 526/125.1 |
| 8,372,927 B2 | 2/2013 | Figueroa et al. | |
| 9,243,090 B2 | 1/2016 | Arriola et al. | |
| 9,349,895 B2 | 5/2016 | Ikenaga et al. | |
| 9,362,436 B2 | 6/2016 | Nanjundiah et al. | |
| 10,457,765 B2 | 10/2019 | Qin et al. | |
| 11,242,421 B2 | 2/2022 | Marks et al. | |
| 2004/0162215 A1 | 8/2004 | Vogel | |
| 2007/0149386 A1 | 6/2007 | Mihan | |
| 2008/0033125 A1 | 2/2008 | Solan et al. | |
| 2008/0249264 A1 | 10/2008 | Hanefeld et al. | |
| 2008/0275189 A1 | 11/2008 | Carnahan et al. | |
| 2008/0311812 A1 | 12/2008 | Arriola et al. | |
| 2009/0209713 A1 | 8/2009 | McGuiness et al. | |
| 2009/0270571 A1 | 10/2009 | Wang et al. | |
| 2010/0048842 A1 | 2/2010 | Figueroa et al. | |
| 2015/0094433 A1 | 4/2015 | Hoang et al. | |
| 2015/0094434 A1 | 4/2015 | Tohi et al. | |
| 2015/0099856 A1 | 4/2015 | Hoang et al. | |
| 2019/0040086 A1 | 2/2019 | Holub et al. | |
| 2021/0054119 A1 | 2/2021 | Senecal et al. | |

FOREIGN PATENT DOCUMENTS

| | | | | |
|---|---|---|---|---|
| CN | 1382147 A | 11/2002 | | |
| CN | 1407996 A | 4/2003 | | |
| CN | 1954005 A | 4/2007 | | |
| CN | 102451758 A | 5/2012 | | |
| DE | 2163956 A1 | 7/1972 | | |
| EP | 0707014 A1 | 4/1996 | | |
| EP | 0573403 B1 | 11/1998 | | |
| EP | 1056752 B1 | 12/2000 | | |
| EP | 1074555 A2 | 2/2001 | | |
| EP | 0856523 A1 | 7/2004 | | |
| EP | 0824112 B1 | 5/2006 | | |
| EP | 1308449 B1 | 3/2008 | | |
| EP | 2468758 A2 | 6/2012 | | |
| EP | 2221328 B1 | 4/2017 | | |
| FR | 2942230 A1 | 8/2010 | | |
| JP | H105-155927 A | 6/1993 | | |
| JP | A-H-6157457 A | 6/1994 | | |
| JP | 11286491 A | 10/1999 | | |
| JP | 2011231292 A | 11/2011 | | |
| KR | 19980070899 A | 10/1998 | | |
| WO | 199735893 A1 | 10/1997 | | |
| WO | 199849212 A1 | 11/1998 | | |
| WO | 199906413 A1 | 2/1999 | | |
| WO | 99/15534 A1 | 4/1999 | | |
| WO | 199941294 A1 | 8/1999 | | |
| WO | 2000053611 A1 | 9/2000 | | |
| WO | 2000063262 A2 | 10/2000 | | |
| WO | 2001023442 A1 | 4/2001 | | |
| WO | WO-0123442 A1 | * | 4/2001 | C08F 10/00 |
| WO | 2001030785 A1 | 5/2001 | | |
| WO | 2001058969 A1 | 8/2001 | | |
| WO | WO-03062208 A1 | * | 7/2003 | C07D 233/80 |
| WO | 2005054254 A1 | 6/2005 | | |
| WO | 2005063829 A1 | 7/2005 | | |
| WO | 2003101936 A1 | 9/2005 | | |
| WO | 2007136494 A2 | 11/2007 | | |
| WO | 2007136496 A2 | 11/2007 | | |
| WO | 2008038173 A2 | 4/2008 | | |
| WO | 2010022228 A2 | 2/2010 | | |
| WO | 2010139684 A1 | 12/2010 | | |
| WO | 2011102989 A1 | 8/2011 | | |
| WO | 2014209927 A1 | 12/2014 | | |
| WO | 2017173080 A1 | 10/2017 | | |

OTHER PUBLICATIONS

Communication pursuant to Article 94(3) EPC dated Mar. 26, 2025, pertaining to EP Patent Application No. 19716696.0, 4 pgs.

Japanese Office Action dated Mar. 25, 2025, pertaining to JP Patent Application No. 2022-562003, 10 pgs.

Chinese Office Action, dated Sep. 21, 2022, pertaining to Chinese Patent Application No. 201980021980.4, 2 pages.

Chinese Search Report, dated Sep. 21, 2022, pertaining to Chinese Patent Application No. 201980021980.4, 3 pages.

Translation of Chinese Office Action and Search Report dated Sep. 30, 2022, pertaining to CN Patent Application No. 201980022075.0, 7 pgs.

Korean Office Action dated Jun. 3, 2024, pertaining to KR Patent Application No. 10-2020-7029426, 9 pgs.

Korean Office Action dated Jun. 3, 2024, pertaining to KR Patent Application No. 10-2020-7029424, 6 pgs.

Korean Office Action dated Jun. 4, 2024, pertaining to KR Patent Application No. 10-2020-7029422, 7 pgs.

Arriola et al., "Catalytic Production of Olefin Block Copolymers via Chain Shuttling Polymerization", Science, 2006,312, 714-719.

U.S. Notice of Allowance and Fee(s) Due dated Apr. 26, 2022 pertaining to U.S. Appl. No. 17/043,304, filed Sep. 29, 2020, pp. 1-13.

Busico, V., "Metal-catalysed olefin polymerisation into the new millennium: a perspective outlook", Dalton Transactions 2009, 8794-8802.

Chinese Office Action, dated Sep. 21, 2022, pertaining to Chinese Patent Application No. 201980021695.2, 7 pages.

Chinese Search Report, dated Sep. 21, 2022, pertaining to Chinese Patent Application No. 201980021695.2, 4 pages.

Delferro et al., "Multinuclear Olefin Polymerization Catalysts", Chem. Rev. 2011, 111, 2450-2485.

European Office Communication pursuant to Article 94(3) EPC dated Jul. 13, 2022 for European Patent Application No. 19716692.9, 5 pgs.

Ewen, J.A., "Propylene Polymerizations with Metallocene/Teal/Trityl Tetrakis (Pentafluorophenyl) Aluminate Mixtures", Catalyst Research Corporation, Houston, Texas, pp. 405-410. Studies in Surface Science and Catalysis 1994, vol. 89.

Galland et al., "13C NMR Determination of the Composition of Linear Low-Density Polyethylene Obtained with [e3- Methallyl-nickel-diimine]PF6 Complex", Macromolecules 1999, 32, 1620-1625.

Gao et al., "Highly Soluble Bis-(Alkyl Substituted Carbenium) Bis-borate as Binuclear Cocatalysts for OlefinPolymerizations", Department of Chemistry, Northwestern University, pp. 1-4, Mar. 30, 2018.

Gao et al., "Supporting Information for Highly Soluble Bis-(Alkyl Substituted Carbenium) Bis-borate as Binuclear Cocatalysts for Olefin Polymerizations", Department of Chemistry, Northwestern University, S1-S26, Mar. 30, 2018.

International Search Report and Written Opinion dated Sep. 13, 2021 pertaining to Int'l Patent Application No. PCT/US2021/031233, 32 pgs.

International Search Report and Written Opinion pertaining to PCT/US2019/023643, dated Jul. 3, 2019.

International Search Report and Written Opinion pertaining to PCT/US2019/024034, dated Jun. 26, 2019.

International Search Report and Written Opinion pertaining to PCT/US2019/024075, dated Jun. 26, 2019.

International Search Report and Written Opinion pertaining to PCT/US2019/024599, dated Jul. 10, 2019.

International Search Report and Written Opinion pertaining to PCT/US2019/024754, dated Jul. 30, 2019.

(56) References Cited

OTHER PUBLICATIONS

Jung et al., "Analysis of Chain Branch of Polyolefins by a New Proton NMR Approach", Anal. Chem. 2016, 38,1516-1520.
Klosin et al., "Development of Group IV Molecular Catalysts for High Temperature Ethylene-a-Olefin Copolymerization Reactions", Acc. Chem. Res. 2015, 48, 2004-2016.
Kraft et al., "Synthesis and Application of Strong Brimsted Acids Generated from the Lewis Acid AI(ORF)3 and an Alcohol", Organometallics2012, 31 (21), 7485-7491.
Krossing, I., "Chemistry with Weakly-Coordinating Fluorinated Alkoxyaluminate Anions: Gas Phase Cations in Condensed Phases?", Coord. Chem. Rev., 2006, 250, 2721-2744.
Krossing, I., "The Facile Preparation of Weakly Coordinating Anions: Structure and Characterisation of Silverpolyfluoroalkoxyaluminates AgAl(ORF)4, Calculation of the Alkoxide lon Affinity", Chem. Eur. J. 2001, 7, 490.
Krossing, Ingo et al. "New reagents to introduce weakly coordinating anions of type AI(ORF)4-: synthesis, structure and characterization of Cs and trityl salts" Journal of Fluorine Chemistry, 2001, pp. 83-90, 112, Elsevier Science B.V.
Lapointe et al., "New Family of Weakly Coordinating Anions", J. Am. Chem. Soc., 2000, 122, 9560-9561.
Li et al., "Catalysl/Cocatalyst Nuclearity Effects in Single-Site Polymerization. Enhanced Polyethylene Branching and r-Olefin Comonomer Enchainment in Polymerizations Mediated by Binuclear Catalysts and Cocatalysts via a New Enchainment Pathway", J. Am. Chem. Soc. 2002, 124, 12725-12741.
Li et al., "Coordination Copolymerization of Severely Encumbered Isoalkenes with Ethylene: Enhanced Enchainment Mediated by Binuclear Catalysts and Cocatalysts", J. Am. Chem. Soc. 2005, 127, 14756-14768.
Li et al., "Nuclearity and cooperativity effects in binuclear catalysts and cocatalysts for olefin polymerization", Proc. Natl. Acad. Sci. U.S. A. 2006, 103, 15295-15302.
Makio et al., "FI Catalysts for Olefin Polymerization—A Comprehensive Treatment", Chem. Rev. 2011, 111, 2363-2449.
Mcguinness et al., "Cocatalyst Influence in Selective Oligomerization: Effect on Activity, Catalyst Stability, and 1-Hexene/1-Octene Selectivity in the Ethylene Trimerization and Tetramerization Reaction", Organometallics 2007, 26 (10), 2561-2569.
Mcinnis et al., "Multinuclear Group 4 Catalysis: Olefin Polymerization Pathways Modified by Strong Metal-Metal Cooperative Effects", Acc. Chem. Res. 2014, 47, 2545-2557.
Metz, Matthew V. et al. "Weakly Coordinating Al-, Nb-, Ta-, Y-, and La-Based Perfluoroaryloxymetalate Anions as Cocatalyst Components for Single-Site Olefin Polymerization" Organometallics, 2002, pp. 3691-3702, 21.
Nakazawa et al., "A Synthetic Two-Spin Quantum Bit: g-Engineered Exchange-Coupled Biradical Designed for Controlled-NOT Gate Operations", Angew. Chem., Int. Ed. 2012, 51, 9860-9864.
Non-final office action Jan. 22, 2022 re: U.S. Appl. No. 17/043,483.
U.S. Office Action dated Aug. 11, 2021 pertaining to U.S. Appl. No. 17/043,304, filed Sep. 29, 2020, 29 pages.
Yano et al., "Influence of activators on ethylene polymerization with -diphenylmethylidene-cyclopentadienyl/-fluorenyl/zirconium dichloride catalysts at high temperature", J. Mol. Catal. A: Chem. 1999, 148, 77.
Pangborn et al., "Safe and Convenient Procedure for Solvent Purification", Organometallics 1996, 15 (5), 1518-1520.
Strauss et al., "LiAl{OC{Ph){CF3)2)4: A Hydrocarbon-Soluble Catalyst for Carbon-Carbon Bond-Forming Reactions" Organometallics 1996, 15, 3776.
Strauss et al., "Relative Lewis Basicities of Six AI(ORF)4y Superweak Anions and the Structures of LiAI{OCH{CF3) 2}4 and [1-Et-3-Me-1,3-C3H3N2]-[Li{Al{OCH{CF3)2)4}2]", Chem. Eur. J. 2001, 7, 503.
Sturzel et al., "From Multisite Polymerization Catalysis to Sustainable Materials and All-Polyolefin Composites", Chem. Rev. 2016, 116, 1398-1433.
Sun et al., "Al-, Nb- and Ta-based Perlluoroaryloxide Anions as Cocatalysts for Metallocene-Mediated Ziegler-Natta Olefin Polymerization", Organometallics, 2000, 1625-1627.
Japanese Office Action dated Mar. 28, 2023, pertaining to JP Patent Application No. 2020-551554, 42 pgs.
Ex Parte Quayle dated Mar. 13, 2023, pertaining to U.S. Appl. No. 17/043,326, 9 pgs.
Examination Report dated Nov. 11, 2022, pertaining to EP Patent Application No. 19716696.0, 6 pgs.
Singpore Substantive Examination Report and Written Opinion dated May 22, 2025, pertaining to Singapore Patent Application No. 11202254731X, 8 pgs.
Chinese Office Action, dated Aug. 15, 2023, pertaining to Chinese Patent Application No. 20180021695.2, 6 pgs.
US Office Action dated Jun. 12, 2023, pertaining to U.S. Appl. No. 17/043,029, 61 pgs.
US Office Action dated Nov. 15, 2023, pertaining to U.S. Appl. No. 17/043,029, 6 pgs.
Korean Office Action dated Oct. 25, 2023, pertaining to KR Patent Application No. 10-2020-7029423, 5 pgs.
Korean Office Action dated Oct. 27, 2023, pertaining to KR Patent Application No. 10-2020-7029422, 14 pgs.
European Office Action dated Dec. 7, 2023, pertaining to EP Patent Application No. 19716696.0, 6 pgs.
Korean Office Action dated Nov. 2, 2023, pertaining to KR Patent Application No. 10-2020-7029424, 15 pgs.
Brazil Technical Report dated Nov. 12, 2024, pertaining to BR Patent Application No. BR112022022454-0, 4 pgs.
Thailand Office Action dated Nov. 18, 2025, pertaining to TH Patent Application No. 2001005526, 11 pgs.
Thailand Office Action dated Nov. 24, 2025, pertaining to TH Patent Application No. 2001005528, 8 pgs.
Korean Office Action dated Dec. 8, 2025, pertaining to KR Patent Application No. 10-2022-7042281, 13 pgs.
Communication pursuant to Article 94(3) EPC dated Aug. 1, 2025, pertaining to EP Patent Application No. 21729376.0, 4 pgs.
Japanese Office Action dated Aug. 28, 2025, pertaining to JP Patent Application No. 2020-5511554, 46 pgs.
Communication pursuant to Article 94(3) EPC dated Feb. 6, 2026, pertaining to EP Patent Application No. 19724276.1, 6 pgs.
Communication pursuant to Article 94(3) EPC dated Apr. 2, 2026, pertaining to EP Patent Application No. 19716696.0, 5 pgs.

* cited by examiner

OLEFIN POLYMERIZATION BIMETALLIC ACTIVATORS

CROSS REFERENCE TO RELATED APPLICATIONS

This application is a national stage entry of PCT/US2021/031233 filed on May 7, 2021, which claims priority to U.S. Provisional Patent Application No. 63/021,419 filed on May 7, 2020, the entire disclosures of which are hereby incorporated by reference.

TECHNICAL FIELD

Embodiments of the present disclosure generally relate to olefin polymerization catalyst systems and processes and, more specifically to olefin polymerization catalyst systems including a Group IV metal-ligand complex and a bimetallic activator or co-catalyst.

BACKGROUND

As part of the catalyst composition in α-olefin polymerization reactions, the activator may have characteristics that are beneficial for the production of the α-olefin polymer and for final polymer compositions. Activator characteristics that increase the production of α-olefin polymers include, but are not limited to: rapid procatalyst activation, high catalyst efficiency, high temperature capability, consistent polymer composition, and selective deactivation.

Olefin-based polymers such as ethylene-based polymers and propylene-based polymers are produced via various catalyst systems. Selection of such catalyst systems can be an important factor contributing to the characteristics and properties of olefin-based polymers. The catalyst systems for producing polyethylene-based polymers may include a chromium-based catalyst system, a Ziegler-Natta catalyst system, or a molecular (either metallocene or non-metallocene) catalyst system.

As part of the catalyst system, the molecular polymerization procatalyst is activated to generate the catalytically active species for polymerization. The catalytic activation achieved by any number of means. One such method employs an activator or co-catalyst that is a Brønsted acid. Brønsted acid salts containing weakly coordinating anions are commonly utilized to activate molecular polymerization procatalysts, particularly such procatalysts comprising Group IV metal complexes. Brønsted acid salts that are fully ionized are capable of transferring a proton to form a cationic derivative of such Group IV metal complexes.

For activators, such as Brønsted acid salts, the cationic component may include cations capable of transferring a hydrogen ion such as ammonium, sulfonium, or phosphonium for example; or oxidizing cations such as ferrocenium, silver, or lead, for example; or highly Lewis acidic cations such as carbonium or silylium, for example.

However, once the cations activate the procatalyst, the activators may remain in the polymer composition. As a result, the cations and anions may affect the polymer composition. Since not all ions diffuse equally, different ions affect the polymer composition differently. In particular, the size of the ion and the charge of the ion, the interaction of the ion with the surrounding medium, and the dissociation energy of the ion with available counterions will affect the ion's ability to diffuse through a surrounding medium, such as a solvent, a gel, or a polymer material.

Conventional olefin polymerization activators include weakly-coordinating or non-coordinating anions. It has been shown that weak coordination of the anion leads to increased catalytic efficiency of the cationic catalyst. However, since the non-nucleophilic character of the non-coordinating anion also increases diffusion, the residual activator anion in the produced polymer will lower the electrical resistance of the polymer, thereby increasing electrical loss, and thereby decreasing the applicability of the produced polymer.

SUMMARY

In a solution polymerization, process catalyst components are generally delivered either as slurries or as solutions. Homogeneous solutions, as opposed to heterogeneous, do not require additional mixing elements to keep the contents uniform. This lessens the complexity associated with delivery of the catalyst component to the reactor. Solutions utilizing aliphatic hydrocarbon solvents like, but not limited to, hexanes, methylcyclohexane, Isopar E™ are generally preferred over the use of toluene and other aromatic solvents as residuals of these aromatic solvents can remain in the resulting polymer limiting the applications in which the polymer can be used.

Good activators for polymerization reactions have characteristics that increase the production of α-olefin polymers; increase the rate of procatalyst activation; increase the overall efficiency of the catalyst to enable the catalyst system to operate at high temperatures; enable the catalyst system to provide consistent polymer composition; and increased solubility of the activator in comparison to anion tetrakis(pentafluorophenyl)borate ($^-B(C_6F_5)_4$). Activators derived from the non-coordinating anion tetrakis(pentafluorophenyl)borate ($^-B(C_6F_5)_4$) capture many of these afore mentioned characteristics. Nevertheless, under typical polymerization reaction conditions, the $^-B(C_6F_5)_4$ anion may remain intact in the final polymer. The presence of an intact activator in the final polymer can be deleterious to the electrical properties of the final polymer.

Activators based on partially hydrolyzed metal trialkyls, such as methylalumoxane (MAO) or modified methylalumoxane (MMAO), for example, decompose more readily than $^-B(C_6F_5)_4$ anion, but suffer from poor high-temperature catalyst efficiency and broader compositional and/or molecular weight drift in the final polymer.

There are ongoing needs for activators that efficiently activate a procatalyst, that are soluble, perform well at high temperature, and do not remain intact in the final polymer. The catalyst systems of this disclosure include, in combination with Group IV metal-ligand complexes as catalysts, activators or co-catalysts that address such needs. In particular, the activators readily react with and activate the Group IV metal-ligand complexes in the production of polyolefin resins, and the polyolefin resins exhibit useful polymer composition and electrical properties. The activators included in the catalyst systems of this disclosure exhibit characteristics, such as, abilities to increase the production of α-olefin polymers, to increase the rate of procatalyst activation, to increase the overall efficiency of the catalyst to enable the catalyst system to operate at high temperatures, to enable the catalyst system to provide consistent polymer composition, and to enable selective deactivation of the activators.

According to one or more embodiments, processes for polymerizing olefins include contacting ethylene and a ($C_3$-$C_{40}$)α-olefin comonomer in the presence of a catalyst system that includes a Group IV metal-ligand complex and a bimetallic activator ionic complex. The bimetallic activator ionic complex includes an anion and a countercation, the anion having a structure according to formula (I):

(I)

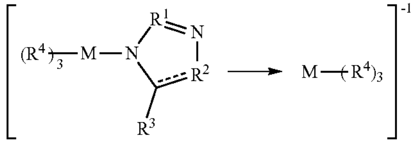

The countercation may be any cation having a formal charge of +1. In formula (I), each M is independently aluminum or boron. $R^1$ is C(H); and $R^2$ is selected from $C(R^L)$ or N, wherein each $R^L$ is independently —H, $(C_1$-$C_{30})$hydrocarbyl, $(C_1$-$C_{30})$heterohydrocarbyl, or halogen-substituted $(C_1$-$C_{30})$hydrocarbyl. $R^3$ is chosen from —H, $(C_1$-$C_{30})$hydrocarbyl, halogen-substituted $(C_1$-$C_{30})$hydrocarbyl, $(C_1$-$C_{30})$heterohydrocarbyl, or $(C_2$-$C_{30})$hydrocarbylene; $R^3$ is optionally connected to $R^2$ to form a ring. When $R^3$ is —H, $R^2$ is N or $C(R^L)$, where $R^L$ is $(C_1$-$C_{30})$hydrocarbyl; and when $R^2$ is C(H), $R^3$ is $(C_1$-$C_{30})$hydrocarbyl.

In formula (I), each $R^4$ is independently selected from the group consisting of a halogen-substituted $(C_1$-$C_{30})$alkyl and radicals having formula (II):

(II)

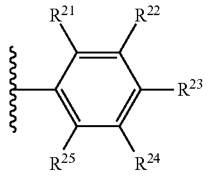

In formula (II), each $R^{21}$, $R^{22}$, $R^{23}$, $R^{24}$, and $R^{25}$ is independently chosen from halogen-substituted $(C_1$-$C_{40})$alkyl, halogen-substituted $(C_6$-$C_{40})$aryl, —H, $—NR^N_2$, $—OR^C$, $—SR^C$, or halogen. Furthermore, when $R^4$ is radical according to formula (II), at least three of $R^{21-25}$ are independently chosen from halogen-substituted $(C_1$-$C_{40})$alkyl, halogen-substituted $(C_6$-$C_{40})$aryl, or —F. Additionally, when $R^4$ is a halogen-substituted $(C_1$-$C_{30})$alkyl, the halogen-substituted $(C_1$-$C_{30})$alkyl is substituted with at least three halogen atoms. Each $R^N$ and each $R^C$ is independently $(C_1$-$C_{30})$hydrocarbyl or —H.

DETAILED DESCRIPTION

Specific embodiments of catalyst systems will now be described. It should be understood that the catalyst systems of this disclosure may be embodied in different forms and should not be construed as limited to the specific embodiments set forth in this disclosure.

Common abbreviations are listed below:

Me: methyl; Et: ethyl; Ph: phenyl; Bn: benzyl; i-Pr: iso-propyl; t-Bu: tert-butyl; t-Oct: tert-octyl (2,4,4-trimethylpentan-2-yl); Tf: trifluoromethane sulfonate; OTf: triflate; $(^tBu^FO)_3Al$: $Al(OC(CF_3)_3)_3$; THF: tetrahydrofuran; $Et_2P$: diethyl ether; $CH_2Cl_2$: dichloromethane; CV: column volume (used in column chromatography); EtOAc: ethyl acetate; $C_6D_6$: deuterated benzene or benzene-d6: $CDCl_3$: deuterated chloroform; $Na_2SO_4$: sodium sulfate; $MgSO_4$: magnesium sulfate; HCl: hydrogen chloride; n-BuLi: butyllithium; t-BuLi: tert-butyllithium; $N_2$: nitrogen gas; PhMe: toluene; PPR: parallel polymerization reactor; MAO: methylaluminoxane; MMAO: modified methylaluminoxane; GC: gas chromatography; LC liquid chromatography; NMR: nuclear magnetic resonance; MS: mass spectrometry; mmol millimoles; mL: milliliters; M: molar; min or mins: minutes; h or hrs: hours; d: days; Rr; retention fraction; TLC; thin layered chromatography; rpm: revolution per minute.

The term "independently selected" is used herein to indicate that the R groups, such as, $R^1$, $R^2$, $R^3$, $R^4$, and $R^5$, can be identical or different (e.g., $R^1$, $R^2$, $R^3$, $R^4$, and $R^5$ may all be substituted alkyls or $R^1$ and $R^2$ may be a substituted alkyl and $R^3$ may be an aryl, etc). A chemical name associated with an R group is intended to convey the chemical structure that is recognized in the art as corresponding to that of the chemical name. Thus, chemical names are intended to supplement and illustrate, not preclude, the structural definitions known to those of skill in the art.

The term "procatalyst" refers to a compound that has catalytic activity when combined with an activator. The term "activator" refers to a compound that chemically reacts with a procatalyst in a manner that converts the procatalyst to a catalytically active catalyst. As used herein, the terms "co-catalyst" and "activator" are interchangeable terms.

When used to describe certain chemical groups containing one or more carbon atoms, a parenthetical expression having the form "$(C_x$-$C_y)$" means that the unsubstituted form of the chemical group has from x carbon atoms to y carbon atoms, inclusive of x and y. For example, a $(C_1$-$C_{50})$alkyl is an alkyl group having from 1 to 50 carbon atoms in its unsubstituted form. In some embodiments and general structures, certain chemical groups may be substituted by one or more substituents such as $R^S$. An $R^S$ substituted chemical group defined using the "$(C_x$-$C_y)$" parenthetical may contain more than y carbon atoms depending on the identity of any groups $R^S$. For example, a "$(C_1$-$C_{50})$alkyl substituted with exactly one group $R^S$, where $R^S$ is phenyl $(—C_6H_5)$" may contain from 7 to 56 carbon atoms. Thus, in general when a chemical group defined using the "$(C_x$-$C_y)$" parenthetical is substituted by one or more carbon atom-containing substituents $R^S$, the minimum and maximum total number of carbon atoms of the chemical group is determined by adding to both x and y the combined sum of the number of carbon atoms from all of the carbon atom-containing substituents $R^S$.

The term "substitution" means that at least one hydrogen atom (—H) bonded to a carbon atom or heteroatom of a corresponding unsubstituted compound or functional group is replaced by a substituent (e.g. $R^S$). The term "persubstitution" means that every hydrogen atom (H) bonded to a carbon atom or heteroatom of a corresponding unsubstituted compound or functional group is replaced by a substituent (e.g., $R^S$). The term "polysubstitution" means that at least two, but fewer than all, hydrogen atoms bonded to carbon atoms or heteroatoms of a corresponding unsubstituted compound or functional group are replaced by a substituent. The term "—H" means a hydrogen or hydrogen radical that is covalently bonded to another atom. "Hydrogen" and "—H" are interchangeable, and unless clearly specified have identical meanings.

The term "halogen-substituted" means that at least one hydrogen atom (—H) bonded to a carbon atom or heteroatom of a corresponding unsubstituted compound or functional group is replaced by a halogen. The term "halogen-substituted" and "halogenated" are interchangeable. The term "perhalogenated" means that every hydrogen atom (—H) bonded to a carbon atom or heteroatom of a corresponding unsubstituted compound or functional group is replaced by a halogen. The term "halogen-substituted" means that at least one hydrogen atom (—H) bonded to a carbon atom or heteroatom of a corresponding unsubstituted compound or functional group is replaced by a halogen atom.

In this disclosure, the term "halogen atom" or "halogen" means the radical of a fluorine atom (F) or chlorine atom (Cl). The term "halide" means anionic form of the halogen atom: fluoride ($F^-$) or chloride ($Cl^-$).

The term "($C_1$-$C_{50}$)hydrocarbyl" means a hydrocarbon radical of from 1 to 50 carbon atoms and the term "($C_1$-$C_{50}$)hydrocarbylene" means a hydrocarbon diradical of from 1 to 50 carbon atoms, in which each hydrocarbon radical and each hydrocarbon diradical is aromatic or non-aromatic, saturated or unsaturated, straight chain or branched chain, cyclic (having three carbons or more, and including mono- and poly-cyclic, fused and non-fused polycyclic, and bicyclic) or acyclic, and substituted by one or more $R^S$ or unsubstituted.

In this disclosure, a ($C_1$-$C_{50}$)hydrocarbyl may be an unsubstituted or substituted ($C_1$-$C_{50}$)alkyl, ($C_3$-$C_{50}$)cycloalkyl, ($C_3$-$C_{20}$)cycloalkyl-($C_1$-$C_{20}$)alkylene, ($C_6$-$C_{40}$)aryl, or ($C_6$-$C_{20}$)aryl-($C_1$-$C_{20}$)alkylene (such as benzyl (—$CH_2$—$C_6H_5$)).

The terms "($C_1$-$C_{50}$)alkyl" and "($C_1$-$C_{18}$)alkyl" mean a saturated straight or branched hydrocarbon radical of from 1 to 50 carbon atoms and a saturated straight or branched hydrocarbon radical of from 1 to 18 carbon atoms, respectively, that is unsubstituted or substituted by one or more $R^S$. Examples of unsubstituted ($C_1$-$C_{50}$)alkyl are unsubstituted ($C_1$-$C_{20}$)alkyl; unsubstituted ($C_1$-$C_{10}$)alkyl; unsubstituted ($C_1$-$C_5$)alkyl; methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted ($C_1$-$C_{40}$)alkyl are substituted ($C_1$-$C_{20}$)alkyl, substituted ($C_1$-$C_{10}$)alkyl, trifluoromethyl, and [$C_{45}$]alkyl. The term "[$C_{45}$]alkyl" means there is a maximum of 45 carbon atoms in the radical, including substituents, and is, for example, a ($C_{27}$-$C_{40}$)alkyl substituted by one $R^S$, which is a ($C_1$-$C_5$)alkyl, respectively. Each ($C_1$-$C_5$)alkyl may be methyl, trifluoromethyl, ethyl, 1-propyl, 1-methylethyl, or 1,1-dimethylethyl.

The term "($C_6$-$C_{50}$)aryl" means an unsubstituted or substituted (by one or more $R^S$) monocyclic, bicyclic, or tricyclic aromatic hydrocarbon radical of from 6 to 40 carbon atoms, of which at least from 6 to 14 of the carbon atoms are aromatic ring carbon atoms. A monocyclic aromatic hydrocarbon radical includes one aromatic ring; a bicyclic aromatic hydrocarbon radical has two rings; and a tricyclic aromatic hydrocarbon radical has three rings. When the bicyclic or tricyclic aromatic hydrocarbon radical is present, at least one of the rings of the radical is aromatic. The other ring or rings of the aromatic radical may be independently fused or non-fused and aromatic or non-aromatic. Examples of unsubstituted ($C_6$-$C_{50}$)aryl include: unsubstituted ($C_6$-$C_{20}$)aryl, unsubstituted ($C_6$-$C_{18}$)aryl; 2-($C_1$-$C_5$)alkyl-phenyl; phenyl; fluorenyl; tetrahydrofluorenyl; indacenyl; hexahydroindacenyl; indenyl; dihydroindenyl; naphthyl; tetrahydronaphthyl; and phenanthrene. Examples of substituted ($C_6$-$C_{40}$)aryl include: substituted ($C_1$-$C_{20}$)aryl; substituted ($C_6$-$C_{18}$)aryl; 2,4-bis([$C_{20}$]alkyl)-phenyl; polyfluorophenyl; pentafluorophenyl; fluoren-9-one-1-yl; and biphenyl.

The term "($C_3$-$C_{50}$)cycloalkyl" means a saturated cyclic hydrocarbon radical of from 3 to 50 carbon atoms that is unsubstituted or substituted by one or more $R^S$. Other cycloalkyl groups (e.g., ($C_x$-$C_y$)cycloalkyl) are defined in an analogous manner as having from x to y carbon atoms and being either unsubstituted or substituted with one or more $R^S$. Examples of unsubstituted ($C_3$-$C_{40}$)cycloalkyl are unsubstituted ($C_3$-$C_{20}$)cycloalkyl, unsubstituted ($C_3$-$C_{10}$)cycloalkyl, cyclopropyl, cyclobutyl, cyclopentyl, cyclohexyl, cycloheptyl, cyclooctyl, cyclononyl, and cyclodecyl. Examples of substituted ($C_3$-$C_{40}$)cycloalkyl are substituted ($C_3$-$C_{20}$)cycloalkyl, substituted ($C_3$-$C_{10}$)cycloalkyl, and 1-fluorocyclohexyl.

Examples of ($C_1$-$C_{50}$)hydrocarbylene include unsubstituted or substituted ($C_6$-$C_{50}$)arylene, ($C_3$-$C_{50}$)cycloalkylene, and ($C_1$-$C_{50}$)alkylene (e.g., ($C_1$-$C_{20}$)alkylene). The diradicals may be on the same carbon atom (e.g., —$CH_2$—) or on adjacent carbon atoms (i.e., 1,2-diradicals), or are spaced apart by one, two, or more than two intervening carbon atoms (e.g., 1,3-diradicals, 1,4-diradicals, etc.). Some diradicals include 1,2-, 1,3-, 1,4-, or an α,ω-diradical, and others a 1,2-diradical. The α,ω-diradical is a diradical that has maximum carbon backbone spacing between the radical carbons. Some examples of ($C_2$-$C_{20}$)alkylene α,ω-diradicals include ethan-1,2-diyl (i.e. —$CH_2CH_2$—), propan-1,3-diyl (i.e. —$CH_2CH_2CH_2$—), 2-methylpropan-1,3-diyl (i.e. —$CH_2CH(CH_3)CH_2$—). Some examples of ($C_6$-$C_{50}$) arylene α,ω-diradicals include phenyl-1,4-diyl, napthalen-2,6-diyl, or napthalen-3,7-diyl.

The term "($C_1$-$C_{50}$)alkylene" means a saturated straight chain or branched chain diradical (i.e., the radicals are not on ring atoms) of from 1 to 50 carbon atoms that is unsubstituted or substituted by one or more $R^S$. Examples of unsubstituted ($C_1$-$C_{50}$)alkylene are unsubstituted ($C_1$-$C_{20}$)alkylene, including unsubstituted —$CH_2CH_2$—, —$(CH_2)_3$—, —$(CH_2)_4$—, —$(CH_2)_5$—, —$(CH_2)_6$—, —$(CH_2)_7$—, —$(CH_2)_8$—, —$CH_2C^*HCH_3$, and —$(CH_2)_4C^*(H)(CH_3)$, in which "C*" denotes a carbon atom from which a hydrogen atom is removed to form a secondary or tertiary alkyl radical. Examples of substituted ($C_1$-$C_{50}$)alkylene are substituted ($C_1$-$C_{20}$)alkylene, —$CF_2$—, —C(O)—, and —$(CH_2)_{14}C(CH_3)_2(CH_2)_5$— (i.e., a 6,6-dimethyl substituted normal-1,20-eicosylene). Since as mentioned previously two $R^S$ may be taken together to form a ($C_1$-$C_{18}$) alkylene, examples of substituted ($C_1$-$C_{50}$)alkylene also include 1,2-bis(methylene)cyclopentane, 1,2-bis(methylene)cyclohexane, 2,3-bis(methylene)-7,7-dimethyl-bicyclo [2.2.1]heptane, and 2,3-bis (methylene)bicyclo [2.2.2]octane.

The term "($C_3$-$C_{50}$)cycloalkylene" means a cyclic diradical of from 3 to 50 carbon atoms that is unsubstituted or substituted by one or more $R^S$. Both radicals of the cyclic diradical are on ring atoms of the cyclic diradical.

The term "heteroatom," refers to an atom other than hydrogen or carbon. Examples of groups containing one or more than one heteroatom include O, S, S(O), $S(O)_2$, $Si(R^C)_2$, $P(R^P)$, $N(R^N)$, —N=$C(R^C)_2$, —$Ge(R^C)_2$—, or —$Si(R^C)$—, where each $R^C$ and each $R^P$ is unsubstituted ($C_1$-$C_{18}$)hydrocarbyl or —H, and where each $R^N$ is unsubstituted ($C_1$-$C_{18}$)hydrocarbyl. The term "heterohydrocarbon" refers to a molecule or molecular framework in which one or more carbon atoms of a hydrocarbon are replaced with a heteroatom. The term "($C_1$-$C_{50}$)heterohydrocarbyl" means a heterohydrocarbon radical of from 1 to 50 carbon atoms, and the term "($C_1$-$C_{50}$)heterohydrocarbylene" means a heterohydrocarbon diradical of from 1 to 50 carbon atoms. The heterohydrocarbon of the ($C_1$-$C_{50}$)heterohydrocarbyl or the ($C_1$-$C_{50}$)heterohydrocarbylene has one or more heteroatoms. The radical of the heterohydrocarbyl may be on a carbon atom or a heteroatom. The two radicals of the heterohydrocarbylene may be on a single carbon atom or on a single heteroatom. Additionally, one of the two radicals of the diradical may be on a carbon atom and the other radical may be on a different carbon atom; one of the two radicals may be on a carbon atom and the other on a heteroatom; or one of the two radicals may be on a heteroatom and the other radical on a different heteroatom. Each $(C_1\text{-}C_{50})$heterohydrocarbyl and $(C_1\text{-}C_{50})$heterohydrocarbylene may be unsubstituted or substituted (by one or more $R^S$), aromatic or non-aromatic, saturated or unsaturated, straight chain or branched chain, cyclic (including mono- and poly-cyclic, fused and non-fused polycyclic), or acyclic.

The $(C_1\text{-}C_{50})$heterohydrocarbyl may be unsubstituted or substituted. Non-limiting examples of the $(C_1\text{-}C_{50})$heterohydrocarbyl include $(C_1\text{-}C_{50})$heteroalkyl, $(C_1\text{-}C_{50})$hydrocarbyl-O—, $(C_1\text{-}C_{50})$hydrocarbyl-S—, $(C_1\text{-}C_{50})$hydrocarbyl-S(O)—, $(C_1\text{-}C_{50})$hydrocarbyl-$S(O)_2$—, $(C_1\text{-}C_{50})$hydrocarbyl-$Si(R^C)_2$—, $(C_1\text{-}C_{50})$hydrocarbyl-$N(R^N)$—, $(C_1\text{-}C_{50})$hydrocarbyl-$P(R^P)$—, $(C_2\text{-}C_{50})$heterocycloalkyl, $(C_2\text{-}C_{19})$heterocycloalkyl-$(C_1\text{-}C_{20})$alkylene, $(C_3\text{-}C_{20})$cycloalkyl-$(C_1\text{-}C_{19})$heteroalkylene, $(C_2\text{-}C_{19})$heterocycloalkyl-$(C_1\text{-}C_{20})$heteroalkylene, $(C_1\text{-}C_{50})$heteroaryl, $(C_1\text{-}C_{19})$heteroaryl-$(C_1\text{-}C_{20})$alkylene, $(C_6\text{-}C_{20})$aryl-$(C_1\text{-}C_{19})$heteroalkylene, or $(C_1\text{-}C_{19})$heteroaryl-$(C_1\text{-}C_{20})$heteroalkylene.

The term "$(C_4\text{-}C_{50})$heteroaryl" means an unsubstituted or substituted (by one or more $R^S$) monocyclic, bicyclic, or tricyclic heteroaromatic hydrocarbon radical of from 4 to 50 total carbon atoms and from 1 to 10 heteroatoms. A monocyclic heteroaromatic hydrocarbon radical includes one heteroaromatic ring; a bicyclic heteroaromatic hydrocarbon radical has two rings; and a tricyclic heteroaromatic hydrocarbon radical has three rings. When the bicyclic or tricyclyc heteroaromatic hydrocarbon radical is present, at least one of the rings in the radical is heteroaromatic. The other ring or rings of the heteroaromatic radical may be independently fused or non-fused and aromatic or non-aromatic. Other heteroaryl groups (e.g., $(C_x\text{-}C_y)$heteroaryl generally, such as $(C_4\text{-}C_{12})$heteroaryl) are defined in an analogous manner as having from x to y carbon atoms (such as 4 to 12 carbon atoms) and being unsubstituted or substituted by one or more than one $R^S$. The monocyclic heteroaromatic hydrocarbon radical is a 5-membered ring or a 6-membered ring.

The 5-membered ring monocyclic heteroaromatic hydrocarbon radical has 5 minus h carbon atoms, where h is the number of heteroatoms and may be 1, 2, or 3; and each heteroatom may be O, S, N, or P. Examples of 5-membered ring heteroaromatic hydrocarbon radicals include pyrrol-1-yl; pyrrol-2-yl; furan-3-yl; thiophen-2-yl; pyrazol-1-yl; isoxazol-2-yl; isothiazol-5-yl; imidazol-2-yl; oxazol-4-yl; thiazol-2-yl; 1,2,4-triazol-1-yl; 1,3,4-oxadiazol-2-yl; 1,3,4-thiadiazol-2-yl; tetrazol-1-yl; tetrazol-2-yl; and tetrazol-5-yl.

The 6-membered ring monocyclic heteroaromatic hydrocarbon radical has 6 minus h carbon atoms, where h is the number of heteroatoms and may be 1 or 2 and the heteroatoms may be N or P. Examples of 6-membered ring heteroaromatic hydrocarbon radicals include pyridine-2-yl; pyrimidin-2-yl; and pyrazin-2-yl.

The bicyclic heteroaromatic hydrocarbon radical can be a fused 5,6- or 6,6-ring system. Examples of the fused 5,6-ring system bicyclic heteroaromatic hydrocarbon radical are indol-1-yl; and benzimidazole-1-yl. Examples of the fused 6,6-ring system bicyclic heteroaromatic hydrocarbon radical are quinolin-2-yl; and isoquinolin-1-yl. The tricyclic heteroaromatic hydrocarbon radical can be a fused 5,6,5-; 5,6,6-; 6,5,6-; or 6,6,6-ring system. An example of the fused 5,6,5-ring system is 1,7-dihydropyrrolo[3,2-f]indol-1-yl. An example of the fused 5,6,6-ring system is 1H-benzo[f]indol-1-yl. An example of the fused 6,5,6-ring system is 9H-carbazol-9-yl. An example of the fused 6,5,6-ring system is 9H-carbazol-9-yl. An example of the fused 6,6,6-ring system is acrydin-9-yl.

The term "$(C_1\text{-}C_{50})$heteroalkyl" means a saturated straight or branched chain radical containing one to fifty carbon atoms, and one or more heteroatom. The term "$(C_1\text{-}C_{50})$heteroalkylene" means a saturated straight or branched chain diradical containing from 1 to 50 carbon atoms and one or more than one heteroatoms. The heteroatoms of the heteroalkyls or the heteroalkylenes may include $Si(R^C)_3$, $Ge(R^C)_3$, $Si(R^C)_2$, $Ge(R^C)_2$, $P(R^P)_2$, $P(R^P)$, $N(R^N)_2$, $N(R^N)$, N, O, $OR^C$, S, $SR^C$, S(O), and $S(O)_2$, wherein each of the heteroalkyl and heteroalkylene groups are unsubstituted or are substituted by one or more $R^S$.

Examples of unsubstituted $(C_2\text{-}C_{40})$heterocycloalkyl include unsubstituted $(C_2\text{-}C_{20})$heterocycloalkyl, unsubstituted $(C_2\text{-}C_{10})$heterocycloalkyl, aziridin-1-yl, oxetan-2-yl, tetrahydrofuran-3-yl, pyrrolidin-1-yl, tetrahydrothiophen-S,S-dioxide-2-yl, morpholin-4-yl, 1,4-dioxan-2-yl, hexahydroazepin-4-yl, 3-oxa-cyclooctyl, 5-thio-cyclononyl, and 2-aza-cyclodecyl.

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents $R^S$, one or more double and/or triple bonds optionally may be present in substituents $R^S$. The term "unsaturated" means containing one or more carbon-carbon double bonds or carbon-carbon triple bonds, or (in heteroatom-containing groups) one or more carbon-nitrogen double bonds, carbon-phosphorous double bonds, or carbon-silicon double bonds, not including double bonds that may be present in substituents $R^S$, if any, or in aromatic rings or heteroaromatic rings, if any.

According to one or more embodiments, processes for polymerizing olefins include contacting ethylene and a $(C_3\text{-}C_{40})\alpha$-olefin comonomer in the presence of a catalyst system that includes a Group IV metal-ligand complex and a bimetallic activator ionic complex. The bimetallic activator ionic complex includes an anion and a countercation, the anion having a structure according to formula (I):

(I)

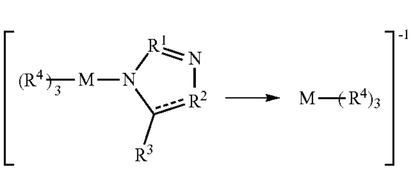

The countercation may be any cation having a formal charge of +1. In formula (I), each M is independently aluminum or boron. $R^1$ is C(H); and $R^2$ is selected from $C(R^L)$ or N, wherein each $R^L$ is independently —H, $(C_1\text{-}C_{30})$hydrocarbyl, $(C_1\text{-}C_{30})$heterohydrocarbyl, or halogen-substituted $(C_1\text{-}C_{30})$hydrocarbyl. $R^3$ is chosen from —H, $(C_1\text{-}C_{30})$hydrocarbyl, halogen-substituted $(C_1\text{-}C_{30})$hydrocarbyl, $(C_1\text{-}C_{30})$heterohydrocarbyl, or $(C_2\text{-}C_{30})$hydrocarbylene; $R^3$ is optionally connected to $R^2$ to form a ring. When $R^3$ is —H, $R^2$ is N or C(Rx), where RX is $(C_1\text{-}C_{30})$hydrocarbyl; and when $R^2$ is C(H), $R^3$ is $(C_1\text{-}C_{30})$hydrocarbyl.

In formula (I), each $R^4$ is independently a radical having formula (II):

(II)

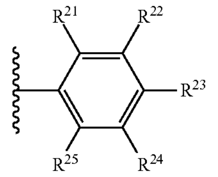

In formula (II), each $R^{21}$, $R^{22}$, $R^{23}$, $R^{24}$, and $R^{25}$ is independently chosen from halogen-substituted $(C_1\text{-}C_{40})$alkyl, halogen-substituted $(C_6\text{-}C_{40})$aryl, —H, $—NR^N_2$, $—OR^C$, $—SR^C$, or halogen. Furthermore, when $R^4$ is a radical according to formula (II), at least three of $R^{21-25}$ are independently chosen from halogen-substituted $(C_1\text{-}C_{40})$alkyl, halogen-substituted $(C_6\text{-}C_{40})$aryl, or —F. Additionally, when $R^4$ is a halogen-substituted $(C_1\text{-}C_{30})$alkyl, the halogen-substituted $(C_1\text{-}C_{30})$alkyl is substituted with at least three halogen atoms. Each $R^N$ and each $R^C$ is independently $(C_1\text{-}C_{30})$hydrocarbyl or —H. In some embodiments, when $R^4$ is a halogen-substituted $(C_1\text{-}C_{30})$alkyl, the halogen-substituted $(C_1\text{-}C_{30})$alkyl is substituted with at least four halogen atoms, at least five halogen atoms, or at least six halogen atoms.

In formula (I), the dotted line between the carbon atom of $C(R^3)$ and $R^2$ may be a double bond or the dotted line may denote resonance.

In embodiments of the catalyst system, in the anion of formula (I), each $R^4$ is a radical having the formula (II), and $R^{21}$, $R^{22}$, $R^{23}$, $R^{24}$, and $R^{25}$ are fluorine.

In some embodiments, $R^1$ is C(H); $R^2$ is C(H); and $R^3$ is $(C_1\text{-}C_{30})$hydrocarbyl or $(C_1\text{-}C_{30})$heterohydrocarbyl. In embodiments, $R^1$ is C(H); $R^2$ is C(H); and $R^3$ is $(C_1\text{-}C_{30})$alkyl. In various embodiments, $R^1$ is C(H); $R^2$ is $C(C_1\text{-}C_{10})$alkyl, and $R_3$ is —H.

In various embodiments, $R^2$ is C(H); and $R^3$ is $(C_1\text{-}C_{10})$alkyl.

In one or more embodiments, $R^1$ is C(H); $R^2$ is C(H); and $R^3$ is methyl, ethyl, propyl, 2-propyl, n-butyl, tert-butyl, 2-methylpropyl, pentyl, hexyl, heptyl, n-octyl, or tert-octyl. In some embodiments, $R^1$ is C(H); $R^2$ is C(H); and $R^3$ is n-octyl or tert-octyl.

In one or more embodiments, $R^3$ is connected to $R^2$ to form a ring, and the anion of the bimetallic activator complex has a structure according to formula (Ia):

(Ia)

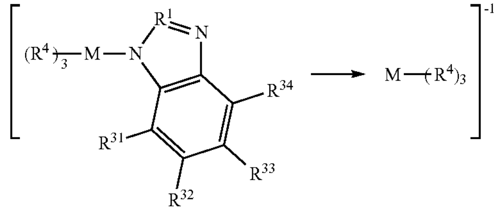

In formula (Ia), $R^{31}$, $R^{32}$, $R^{33}$, and $R^{34}$ are independently a $(C_1\text{-}C_{30})$hydrocarbyl, $(C_1\text{-}C_{30})$heterohydrocarbyl, or —H; and $R^1$, R, and M are as defined in formula (I).

In some embodiments, the bimetallic activator complex according to formula (Ia), each $R^4$ is $—C_6F_5$.

In embodiments, at least one of $R^{32}$ and $R^{33}$ is $—CH_2Si(R^C)_3$, where each $R^C$ is independently $(C_1\text{-}C_{10})$alkyl. In one or more embodiments, at least one of $R^{32}$ and $R^{33}$ is $—CH_2Si(CH_3)_2(R^C)$, where $R^C$ is independently $(C_1\text{-}C_{10})$alkyl. In some embodiments, at least one of $R^{32}$ and $R^{33}$ is $—CH_2Si(CH_3)_2(C_8H_{17})$.

In some embodiments, each M is boron.

In illustrative embodiments, the catalyst systems may include a bimetallic activator ionic complex comprising an anion and a countercation, in which the anion is according to formula (I). The illustrative embodiments include the anionic structure complexed with a countercation as described in this disclosure, and have the following structure:

Activator 1

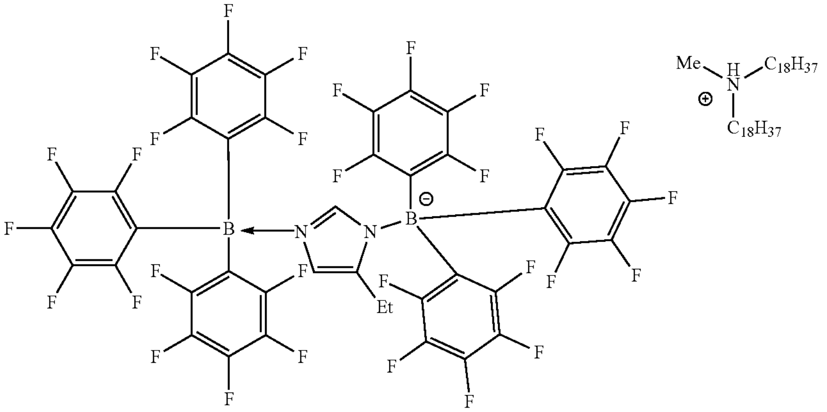

-continued

Activator 2

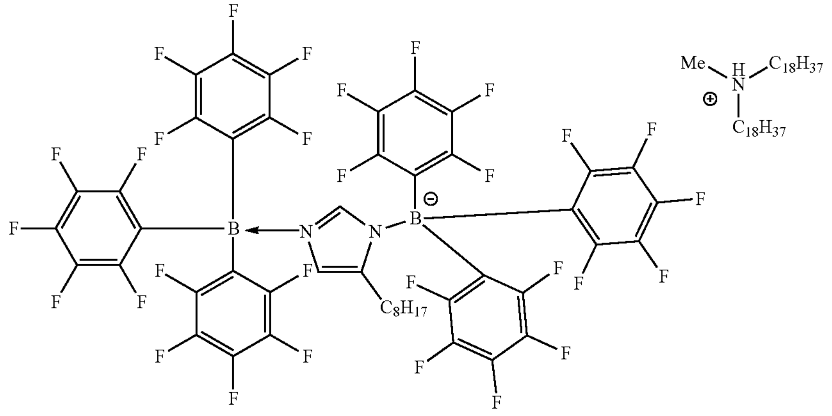

Activator 3

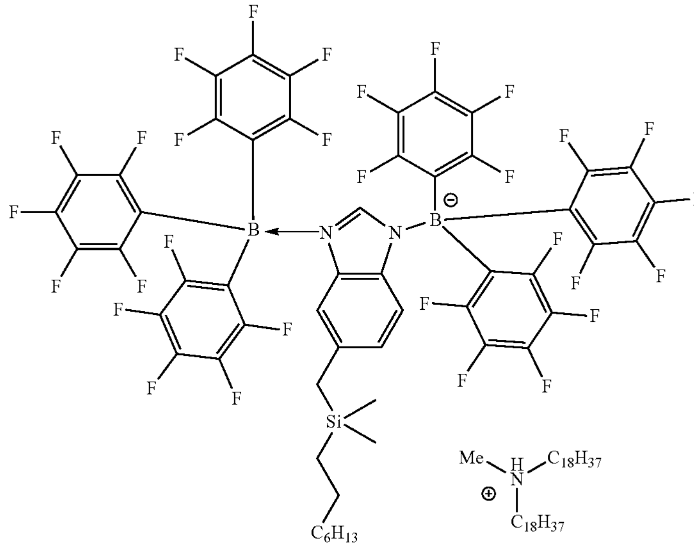

Polymeric Electrical Properties

The electrical insulating efficiency of a medium, such as a polymer material, may be assessed in view of the electrical resistance of the medium and the electrical loss of the medium. Electrical loss lowers the efficiency by which the insulating medium electrically insulates in the presence of an electric field. The resistance of the insulating medium should be as high as possible for both alternating current (AC) and direct current (DC) systems, because the resistance is inversely related to the power or electric loss.

In a DC system such as a photovoltaic device encapsulated in an insulating medium such as a polymer material, electric loss manifests as the leakage of current from the encapsulated device through the encapsulant to the external environment. This current (I) is directly related to the voltage (V) across the insulating medium and inversely related to the resistance (R) of the insulating medium according to the equation $I=V\times R^{-1}$. Therefore for a given operating voltage, the higher the resistance, the lower the leakage current.

In an AC system including an insulating medium such as cable insulation, electric loss manifests as the absorption of energy by the insulating medium in the presence of an electric field. Measured in power (P), this loss is determined by the equation $P=V^2\times\omega\times C\times\varepsilon'\times\tan\delta$ where ω is the angular frequency (e.g. 50 or 60 Hz), $\varepsilon^{-1}$ is the dielectric constant, C is the capacitance, and tan δ is the dissipation factor, $\tan\delta=(C\times R\times\omega)^{-1}$, resulting in the equation $P=V^2\times\varepsilon'\times R^{-1}$. Since the resistance is inversely related to the power loss, the higher the resistance, the lower the power loss.

The electrical resistance of a medium is generally decreased as a result of ionic diffusion caused by an external electric field. In a system in which ionic diffusion dominates the electrical response, the resistance is related to the diffusing ions according to the equation $R=\varepsilon'\times\varepsilon_0\times C^{-1}\times q^{-1}\times N^{-1}\times\mu^{-1}$ where $\varepsilon_0$ is the permittivity of vacuum ($8.854\times10^{-12}$ $F\cdot m^{-1}$), q is the charge of the ion, N is the concentration of the ion, and p is the electrical mobility of the ion. Since increased resistance decreases energy loss and a decrease in ion concentration increases resistance, a reduction in the concentration of ions diffusing through the medium or a reduction of their electrical mobility (e.g. lower solubility) decreases energy loss.

An ability of an ion to diffuse through a given medium is influenced by the size of the ion, the charge of the ion, the interaction of the ion with the surrounding medium, and the ion's dissociation energy with available counterions. Since not all ions diffuse equally through the given medium, when the medium is a polymer, the diffusivity of the ions generally affects the insulation ability of the polymer. Without intending to be bound by theory, it is believed that produced polymers of the catalyst systems of this disclosure have desirable electrical properties such as decreased electrical loss, because the anions of the ionic bimetallic activator complex of formula (I) are less able to diffuse through the produced polymer and/or are at a lower concentration in the final product due to intentional degradation.

Catalyst System Components

The catalyst system includes a procatalyst. The procatalyst may be chosen from a Group IV metal-ligand complex such as a titanium (Ti) metal-ligand complex, a zirconium (Zr) metal-ligand complex, or a hafnium (Hf metal-ligand complex. In one or more embodiments, the Group IV metal-ligand complex includes a bis-biphenylphenoxy Group IV metal-ligand complex, a procatalyst, which may be rendered catalytically active upon contact with the activators of this disclosure.

According to some embodiments, the bis-biphenylphenoxy Group IV metal-ligand complex has a structure according to formula (X):

(X)

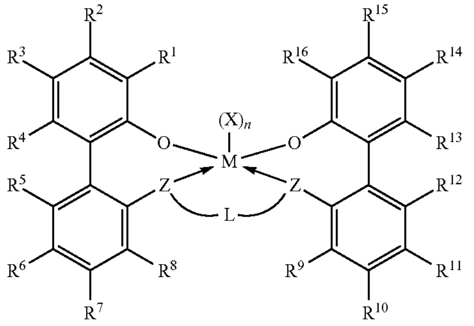

In formula (X), M is a metal chosen from titanium, zirconium, or hafnium, the metal being in a formal oxidation state of +2, +3, or +4. Subscript n of (X)n is 0, 1, or 2. When subscript n is 1, X is a monodentate ligand or a bidentate ligand, and when subscript n is 2, each X is a monodentate ligand. Each Z is independently chosen from —O—, —S—, —N($R^N$)—, or —P($R^P$)—; $R^2$-4, $R^{5-8}$, $R^{9-12}$ and $R^{13-15}$ are independently selected from the group consisting of —H, ($C_1$-$C_{40}$)hydrocarbyl, ($C_1$-$C_{40}$)heterohydrocarbyl, —Si($R^C$)$_3$, —Ge($R^C$)$_3$, P($R^P$)$_2$, —N($R^N$)$_2$, —O$R^C$, —S$R^C$, —$NO_2$, —CN, —$CF_3$, $R^c$S(O)—, $R^c$S(O)$_2$—, —N═C($R^C$)$_2$, $R^C$C(O)O—, $R^C$OC(O)—, $R^C$C(O)N(R)—, ($R^C$)$_2$NC(O)—, and halogen. $R^1$ and $R^{16}$ are selected from radicals having formula (XI), radicals having formula (XII), and radicals having formula (XIII):

(XI)

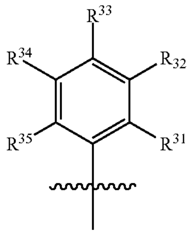

-continued (XII)

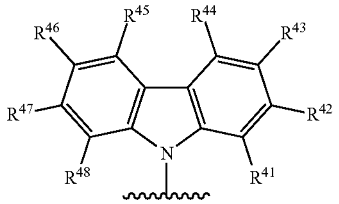

(XIII)

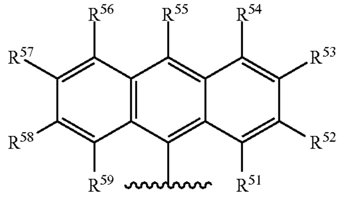

In formulas (XI), (XII), and (XIII), each of $R^{31-35}$, $R^{41-48}$, and $R^{51-59}$ is independently chosen from —H, ($C_1$-$C_{40}$) hydrocarbyl, ($C_1$-$C_{40}$)heterohydrocarbyl, —Si($R^C$)$_3$, —Ge ($R^C$)$_3$, P($R^P$)$_2$, —N($R^N$)$_2$, —O$R^C$—S$R^C$—$NO_2$, —CN, —$CF_3$, $R^c$S(O)—, $R^c$S(O)$_2$—, ($R^C$)$_2$C═N—, $R^C$C(O)O—, $R^C$OC(O)—, RCC(O)N($R^N$)_, ($R^C$)$_2$NC(O)—, OR HALOGEN.

In one or more embodiments, each X can be a monodentate ligand that, independently from any other ligands X, is a halogen, unsubstituted ($C_1$-$C_{20}$)hydrocarbyl, unsubstituted [($C_1$-$C_{20}$)hydrocarbyl]C(O)O—, or $R^K R^L$N—, wherein each of $R^K$ and $R^L$ independently is an unsubstituted($C_1$-$C_{20}$) hydrocarbyl.

Illustrative metal-ligand complexes according to formula (X) include, for example:

(2',2"-(propane-1,3-diylbis(oxy))bis(5'-chloro-3-(3,6-di-tert-octyl-9H-carbazol-9-yl)-3'-methyl-5-(2,4,4-trimethylpentan-2-yl)biphenyl-2-ol)dimethyl-hafnium;

(2',2"-(propane-1,3-diylbis(oxy))bis(3-(3,6-di-tert-butyl-9H-carbazol-9-yl)-3'-chloro-5-(2,4,4-trimethylpentan-2-yl)biphenyl-2-ol)dimethyl-hafnium;

(2',2"-(propane-1,3-diylbis(oxy))bis(3'-chloro-3-(3,6-di-tert-butyl-9H-carbazol-9-yl)-5'-fluoro-5-(2,4,4-trimethylpentan-2-yl)biphenyl-2-ol)dimethyl-hafnium;

(2',2"-(propane-1,3-diylbis(oxy))bis(3-(3,6-di-tert-butyl-9H-carbazol-9-yl)-3'-methyl-5-(2,4,4-trimethylpentan-2-yl)biphenyl-2-ol)dimethyl-hafnium;

(2',2"-(propane-1,3-diylbis(oxy))bis(5'-cyano-3-(3,6-di-tert-butyl-9H-carbazol-9-yl)-3'-methyl-5-(2,4,4-trimethylpentan-2-yl)biphenyl-2-ol)dimethyl-hafnium;

(2',2"-(propane-1,3-diylbis(oxy))bis(5'-dimethylamino-3-(3,6-di-tert-butyl-9H-carbazol-9-yl)-3'-methyl-5-(2,4,4-trimethylpentan-2-yl)biphenyl-2-ol)dimethyl-hafnium;

(2',2"-(propane-1,3-diylbis(oxy))bis(3',5'-dimethyl-3-(3,6-di-tert-butyl-9H-carbazol-9-yl)-5-(2,4,4-trimethylpentan-2-yl)biphenyl-2-ol)dimethyl-hafnium;

(2',2"-(propane-1,3-diylbis(oxy))bis(5'-chloro-3-(3,6-di-tert-butyl-9H-carbazol-9-yl)-3'-ethyl-5-(2,4,4-trimethylpentan-2-yl)biphenyl-2-ol)dimethyl-hafnium;

(2',2"-(propane-1,3-diylbis(oxy))bis(3-(3,6-di-tert-butyl-9H-carbazol-9-yl)-3'-methyl-5'-tert-butyl-5-(2,4,4-trimethylpentan-2-yl)biphenyl-2-ol)dimethyl-hafnium;

(2',2"-(propane-1,3-diylbis(oxy))bis(3-(3,6-di-tert-butyl-9H-carbazol-9-yl)-5'-fluoro-3'-methyl-5-(2,4,4-trimethylpentan-2-yl)biphenyl-2-ol)dimethyl-hafnium;

(2',2"-(propane-1,3-diylbis(oxy))bis(3-(9H-carbazol-9-yl)-5'-chloro-3'-methyl-5-(2,4,4-trimethylpentan-2-yl)biphenyl-2-ol)dimethyl-hafnium;

(2',2"-(propane-1,3-diylbis(oxy))bis(3-(3,6-di-tert-butyl-9H-carbazol-9-yl)-3'-methyl-5'-trifluoromethyl-5-(2,4,4-trimethylpentan-2-yl)biphenyl-2-ol)dimethyl-hafnium;
(2',2"-(2,2-dimethyl-2-silapropane-1,3-diylbis(oxy))bis(3',5'-dichloro-3-(3,6-di-tert-butyl-9H-carbazol-9-yl)-5-(2,4,4-trimethylpentan-2-yl)biphenyl-2-ol)dimethyl-hafnium;
(2'2"-(2,2-dimethyl-2-silapropane-1-diylbis(oxy))bis(5'-chloro-3-(3,6-di-tert-butyl-9 carbazol-9-yl)-3'-methyl-5-(2,4,4 rimethylpentan-2-yl)biphenyl-2-ol)dimethyl-hafnium;
(2',2"-(propane-1,3-diylbis(oxy))bis(3'-bromo-5'-chloro-3-(3,6-di-tert-butyl-9H-carbazol-9-yl)-5-(2,4,4-trimethylpentan-2-yl)biphenyl-2-ol)dimethyl-hafnium;
(2',2"-(propane-1,3-diylbis(oxy))-(5'-chloro-3-(3,6-di-tert-butyl-9H-carbazol-9-yl)-3'-fluoro-5-(2,4,4-trimethylpentan-2-yl)biphenyl-2-ol)-(3",5"-dichloro-3-(3,6-di-tert-butyl-9H-carbazol-9-yl)-5-(2,4,4-trimethylpentan-2-yl) biphenyl-2-ol)dimethyl-hafnium;
(2',2"-(propane-1,3-diylbis(oxy))bis(3-(3,6-di-tert-butyl-9H-carbazol-9-yl)-5'-fluoro-3'-trifluoromethyl-5-(2,4,4-trimethylpentan-2-yl)biphenyl-2-ol)dimethyl-hafnium;
(2',2"-(butane-1,4-diylbis(oxy))bis(5'-chloro-3-(3,6-di-tert-butyl-9H-carbazol-9-yl)-3'-methyl-5-(2,4,4-trimethylpentan-2-yl)biphenyl-2-ol)dimethyl-hafnium;
(2',2"-(ethane-1,2-diylbis(oxy))bis(5'-chloro-3-(3,6-di-tert-butyl-9H-carbazol-9-yl)-3'-methyl-5-(2,4,4-trimethylpentan-2-yl)biphenyl-2-ol)dimethyl-hafnium;
(2',2"-(propane-1,3-diylbis(oxy))bis(5'-chloro-3-(3,6-di-tert-butyl-9H-carbazol-9-yl)-3'-methyl-5-(2,4,4-trimethylpentan-2-yl)biphenyl-2-ol)dimethyl-zirconium;
(2',2"-(propane-1,3-diylbis(oxy))bis(3-(3,6-di-tert-butyl-9H-carbazol-9-yl)-3',5'-dichloro-5-(2,4,4-trimethylpentan-2-yl)biphenyl-2-ol)dimethyl-titanium; and
(2',2"-(propane-1,3-diylbis(oxy))bis(5'-chloro-3-(3,6-di-tert-butyl-9H-carbazol-9-yl)-3'-methyl-5-(2,4,4-trimethylpentan-2-yl)biphenyl-2-ol)dimethyl-titanium.

Other bis-biphenylphenoxy Group IV metal-ligand complexes that may be used in combination with the bimetallic activators in the catalyst systems of this disclosure will be apparent to those skilled in the art.

In one or more embodiments, the Group IV metal-ligand complex includes a constrained-geometry Group IV complex. Illustrative constrained geometry Group IV complexes that may be employed in embodiments include:

cyclopentadienyltitaniumtrimethyl;
cyclopentadienyltitaniumtriethyl;
cyclopentadienyltitaniumtriisopropyl;
cyclopentadienyltitaniumtriphenyl;
cyclopentadienyltitaniumtribenzyl;
cyclopentadienyltitanium-2,4-dimethylpentadienyl;
cyclopentadienyltitanium-2,4-dimethylpentadienyl·triethylphosphine;
cyclopentadienyltitanium-2,4-dimethylpentadienyl·trimethylphosphine;
cyclopentadienyltitaniumdimethylmethoxide;
cyclopentadienyltitaniumdimethylchloride;
pentamethylcyclopentadienyltitaniumtrimethyl;
indenyltitaniumtrimethyl;
indenyltitaniumtriethyl;
indenyltitaniumtripropyl;
indenyltitaniumtriphenyl;
tetrahydroindenyltitaniumtribenzyl;
pentamethylcyclopentadienyltitaniumtriisopropyl;
pentamethylcyclopentadienyltitaniumtribenzyl;
pentamethylcyclopentadienyltitaniumdimethylmethoxide;
pentamethylcyclopentadienyltitaniumdimethylchloride;
bis($\eta^5$-2,4-dimethylpentadienyl)titanium;
bis($\eta^5$-2,4-dimethylpentadienyl)titanium·trimethylphosphine;
bis($\eta^5$-2,4-dimethylpentadienyl)titanium·triethylphosphine;
octahydrofluorenyltitaniumtrimethyl;
tetrahydroindenyltitaniumtrimethyl;
tetrahydrofluorenyltitaniumtrimethyl;
(tert-butylamido)(1,1-dimethyl-2,3,4,9,10-q-1,4,5,6,7,8-hexahydronaphthalenyl)dimethylsilanetitaniumdimethyl;
(tert-butylamido)(1,1,2,3-tetramethyl-2,3,4,9,10-q-1,4,5,6,7,8-hexahydronaphthalenyl)dimethylsilanetitaniumdimethyl;
(tert-butylamido)(tetramethyl-$\eta^5$-cyclopentadienyl) dimethylsilanetitanium dibenzyl;
(tert-butylamido)(tetramethyl-$\eta^5$-cyclopentadienyl)dimethylsilanetitanium dimethyl;
(tert-butylamido)(tetramethyl-$\eta^5$-cyclopentadienyl)-1,2-ethanediyltitanium dimethyl;
(tert-butylamido)(tetramethyl-$\eta^5$-indenyl)dimethylsilanetitanium dimethyl;
(tert-butylamido)(tetramethyl-$\eta^5$-cyclopentadienyl)dimethylsilane titanium (III) 2-(dimethylamino)benzyl;
(tert-butylamido)(tetramethyl-$\eta^5$-cyclopentadienyl)dimethylsilanetitanium (III) allyl;
(tert-butylamido)(tetramethyl-$\eta^5$-cyclopentadienyl)dimethylsilanetitanium (III) 2,4-dimethylpentadienyl;
(tert-butylamido)(tetramethyl-$\eta^5$-cyclopentadienyl)dimethylsilanetitanium (II) 1,4-diphenyl-1,3-butadiene;
(tert-butylamido)(tetramethyl-$\eta^5$-cyclopentadienyl)dimethylsilanetitanium (II) 1,3-pentadiene;
(tert-butylamido)(2-methylindenyl)dimethylsilanetitanium (II) 1,4-diphenyl-1,3-butadiene;
(tert-butylamido)(2-methylindenyl)dimethylsilanetitanium (II) 2,4-hexadiene;
(tert-butylamido)(2-methylindenyl)dimethylsilanetitanium (IV) 2,3-dimethyl-1,3-butadiene;
(tert-butylamido)(2-methylindenyl)dimethylsilanetitanium (IV) isoprene;
(tert-butylamido)(2-methylindenyl)dimethylsilanetitanium (IV) 1,3-butadiene;
(tert-butylamido)(2,3-dimethylindenyl)dimethylsilanetitanium (IV) 2,3-dimethyl-1,3-butadiene;
(tert-butylamido)(2,3-dimethylindenyl)dimethylsilanetitanium (IV) isoprene;
(tert-butylamido)(2,3-dimethylindenyl)dimethylsilanetitanium (IV) dimethyl;
(tert-butylamido)(2,3-dimethylindenyl)dimethylsilanetitanium (IV) dibenzyl;
(tert-butylamido)(2,3-dimethylindenyl)dimethylsilanetitanium (IV) 1,3-butadiene;
(tert-butylamido)(2,3-dimethylindenyl)dimethylsilanetitanium (II) 1,3-pentadiene;
(tert-butylamido)(2,3-dimethylindenyl)dimethylsilanetitanium (II) 1,4-diphenyl-1,3-butadiene;
(tert-butylamido)(2-methylindenyl)dimethylsilanetitanium (II) 1,3-pentadiene;
(tert-butylamido)(2-methylindenyl)dimethylsilanetitanium (IV) dimethyl;
(tert-butylamido)(2-methylindenyl)dimethylsilanetitanium (IV) dibenzyl;
(tert-butylamido)(2-methyl-4-phenylindenyl)dimethylsilanetitanium (II) 1,4-diphenyl-1,3-butadiene;
(tert-butylamido)(2-methyl-4-phenylindenyl)dimethylsilanetitanium (II) 1,3-pentadiene;

(tert-butylamido)(2-methyl-4-phenylindenyl)dimethylsilanetitanium (II) 2,4-hexadiene;
(tert-butylamido)(tetramethyl-$\eta^5$-cyclopentadienyl)dimethyl-silanetitanium (IV) 1,3-butadiene;
(tert-butylamido)(tetramethyl-$\eta^5$-cyclopentadienyl)dimethylsilanetitanium (IV) 2,3-dimethyl-1,3-butadiene;
(tert-butylamido)(tetramethyl-$\eta^5$-cyclopentadienyl)dimethylsilanetitanium (IV) isoprene;
(tert-butylamido)(tetramethyl-$\eta^5$-cyclopentadienyl)dimethyl-silanetitanium (II) 1,4-dibenzyl-1,3-butadiene;
(tert-butylamido)(tetramethyl-$\eta^5$-cyclopentadienyl)dimethylsilanetitanium (II) 2,4-hexadiene;
(tert-butylamido)(tetramethyl-$\eta^5$-cyclopentadienyl)dimethyl-silanetitanium (II) 3-methyl-1,3-pentadiene;
(tert-butylamido)(2,4-dimethylpentadien-3-yl)dimethylsilanetitaniumdimethyl;
(tert-butylamido)(6,6-dimethylcyclohexadienyl)dimethylsilanetitaniumdimethyl;
(tert-butylamido)(1,1-dimethyl-2,3,4,9,10-q-1,4,5,6,7,8-hexahydronaphthalen-4-yl)dimethylsilanetitaniumdimethyl;
(tert-butylamido)(1,1,2,3-tetramethyl-2,3,4,9,10-r-1,4,5,6,7,8-hexahydronaphthalen-4-yl)dimethylsilanetitaniumdimethyl;
(tert-butylamido)(tetramethyl-$\eta^5$-cyclopentadienyl methylphenylsilanetitanium (IV) dimethyl;
(tert-butylamido)(tetramethyl-$\eta^5$-cyclopentadienyl methylphenylsilanetitanium (II) 1,4-diphenyl-1,3-butadiene;
1-(tert-butylamido)-2-(tetramethyl-$\eta^5$-cyclopentadienyl) ethanediyltitanium (IV) dimethyl;
1-(tert-butylamido)-2-(tetramethyl-$\eta^5$-cyclopentadienyl) ethanediyl-titanium (II) 1,4-diphenyl-1,3-butadiene;

Other catalysts, especially catalysts containing one or more other Group IV metal-complexes not specifically listed above, will be apparent to those skilled in the art.

The catalyst systems of this disclosure may include co-catalysts or activators in addition to the bimetallic activator ionic complex having the anion of formula (I) and a countercation. Such additional co-catalysts may include, for example, tri(hydrocarbyl)aluminum compounds having from 1 to 10 carbons in each hydrocarbyl group, an oligomeric or polymeric alumoxane compound, di(hydrocarbyl)(hydrocarbyloxy)aluminums compound having from 1 to 20 carbons in each hydrocarbyl or hydrocarbyloxy group, or mixtures of the foregoing compounds. These aluminum compounds are usefully employed for their beneficial ability to scavenge impurities such as oxygen, water, and aldehydes from the polymerization mixture.

The di(hydrocarbyl)(hydrocarbyloxy)aluminum compounds that may be used in conjunction with the activators described in this disclosure correspond to the formula $T^1_2AlOT^2$ or $T_1Al(OT^2)_2$ wherein $T^1$ is a secondary or tertiary ($C_3$-$C_6$)alkyl, such as isopropyl, isobutyl or tert-butyl; and $T^2$ is a alkyl substituted ($C_6$-$C_{30}$)aryl radical or aryl substituted ($C_1$-$C_{30}$)alkyl radical, such as 2,6-di(tert-butyl)-4-methylphenyl, 2,6-di(tert-butyl)-4-methylphenyl, 2,6-di(tert-butyl)-4-methyltolyl, or 4-(3',5'-di-tert-butyltolyl)-2,6-di-tert-butylphenyl.

Additional examples of aluminum compounds include [$C_6$]trialkyl aluminum compounds, especially those wherein the alkyl groups are ethyl, propyl, isopropyl, n-butyl, isobutyl, pentyl, neopentyl, or isopentyl, dialkyl(aryloxy) aluminum compounds containing from 1-6 carbons in the alkyl group and from 6 to 18 carbons in the aryl group (especially (3,5-di(t-butyl)-4-methylphenoxy)diisobutylaluminum), methylalumoxane, modified methylalumoxane and diisobutylalumoxane.

In the catalyst systems according to embodiments of this disclosure, the molar ratio of the bimetallic activator ionic complex to Group IV metal-ligand complex may be from 1:10,000 to 1000:1, such as, for example, from 1:5000 to 100:1, from 1:100 to 100:1 from 1:10 to 10:1, from 1:5 to 1:1, or from 1:1.5 to 1:1. The catalyst systems may include combinations of one or more bimetallic activator ionic complex described in this disclosure.

Polyolefins

The catalytic systems described in the preceding paragraphs are utilized in the polymerization of olefins, primarily ethylene and propylene. In some embodiments, there is only a single type of olefin or α-olefin in the polymerization scheme, creating a homopolymer. However, additional α-olefins may be incorporated into the polymerization procedure. The additional α-olefin co-monomers typically have no more than 20 carbon atoms. For example, the α-olefin co-monomers may have 3 to 10 carbon atoms or 3 to 8 carbon atoms. Exemplary α-olefin co-monomers include, but are not limited to, propylene, 1-butene, 1-pentene, 1-hexene, 1-heptene, 1-octene, 1-nonene, 1-decene, 4-methyl-1-pentene, 5-ethyldiene-2-norbornene, and 5-vinyl-2-norbornene. For example, the one or more α-olefin co-monomers may be selected from the group consisting of propylene, 1-butene, 1-hexene, and 1-octene; or in the alternative, from the group consisting of 1-hexene and 1-octene.

Ethylene-based polymers, for example homopolymers and/or interpolymers (including copolymers) of ethylene and optionally one or more co-monomers such as α-olefins, may comprise from at least 50 mole percent (mol %) monomer units derived from ethylene. All individual values and subranges encompassed by "from at least 50 mol %" are disclosed herein as separate embodiments; for example, the ethylene-based polymers, homopolymers and/or interpolymers (including copolymers) of ethylene and optionally one or more co-monomers such as α-olefins may comprise at least 60 mol % monomer units derived from ethylene; at least 70 mol % monomer units derived from ethylene; at least 80 mol % monomer units derived from ethylene; or from 50 to 100 mol % monomer units derived from ethylene; or from 80 to 100 mol % units derived from ethylene.

In some embodiments of the ethylene-based polymer, the ethylene-based polymers may comprise an amount of ($C_3$-$C_{40}$)α-olefin. The amount of ($C_3$-$C_{40}$)α-olefin is less than 50 mol %. In some embodiments, the ethylene-based polymer may include at least 0.5 mol % to 25 mol % of ($C_3$-$C_{40}$)α-olefin; and in further embodiments, the ethylene-based polymer may include at least 5 mol % to 10 mol %. In some embodiments, the ($C_3$-$C_{40}$)α-olefin is 1-octene.

Any conventional polymerization process, in combination with a catalyst system according to embodiments of this disclosure, may be used to produce the ethylene-based polymers. Such conventional polymerization processes include, but are not limited to, solution polymerization processes, gas phase polymerization processes, slurry phase polymerization processes, and combinations thereof using one or more conventional reactors such as loop reactors, isothermal reactors, fluidized bed gas phase reactors, stirred tank reactors, batch reactors in parallel, series, or any combinations thereof, for example.

In one embodiment, ethylene-based polymer may be produced via solution polymerization in a dual reactor system, for example a dual loop reactor system, wherein ethylene and optionally one or more α-olefins are polymerized in the presence of the catalyst system, as described herein, and optionally one or more co-catalysts. In another embodiment, the ethylene-based polymer may be produced via solution polymerization in a dual reactor system, for example a dual loop reactor system, wherein ethylene and optionally one or more α-olefins are polymerized in the presence of the catalyst system in this disclosure, and as described herein, and optionally one or more other catalysts. The catalyst system, as described herein, can be used in the first reactor, or second reactor, optionally in combination with one or more other catalysts. In one embodiment, the ethylene-based polymer may be produced via solution polymerization in a dual reactor system, for example a dual loop reactor system, wherein ethylene and optionally one or more α-olefins are polymerized in the presence of the catalyst system, as described herein, in both reactors.

In another embodiment, the ethylene-based polymer may be produced via solution polymerization in a single reactor system, for example a single loop reactor system, in which ethylene and optionally one or more α-olefins are polymerized in the presence of the catalyst system, as described within this disclosure.

The polymer process may further include incorporating one or more additives. Such additives include, but are not limited to, antistatic agents, color enhancers, dyes, lubricants, pigments, primary antioxidants, secondary antioxidants, processing aids, UV stabilizers, and combinations thereof. The ethylene-based polymers may contain any amounts of additives. The ethylene-based polymers may comprise from about 0 to about 10 percent by the combined weight of such additives, based on the weight of the ethylene-based polymers and the one or more additives. The ethylene-based polymers may further comprise fillers, which may include, but are not limited to, organic or inorganic fillers. The ethylene-based polymers may contain from about 0 to about 20 weight percent fillers such as, for example, calcium carbonate, talc, or $Mg(OH)_2$, based on the combined weight of the ethylene-based polymers and all additives or fillers. The ethylene-based polymers may further be blended with one or more polymers to form a blend.

In some embodiments, a polymerization process for producing an ethylene-based polymer may include polymerizing ethylene and at least one additional α-olefin in the presence of a catalyst system, wherein the catalyst system incorporates at least one metal-ligand complex and a bimetallic activator ionic complex. The polymer resulting from such a catalyst system that incorporates the metal-ligand complex and the bimetallic activator ionic complex may have a density according to ASTM D792 (incorporated herein by reference in its entirety) from 0.850 g/$cm^3$ to 0.950 g/$cm^3$, from 0.870 g/$cm^3$ to 0.920 g/$cm^3$, from 0.870 g/$cm^3$ to 0.910 g/$cm^3$, or from 0.870 g/$cm^3$ to 0.900 g/$cm^3$, for example.

In another embodiment, the polymer resulting from the catalyst system that includes the metal-ligand complex and a bimetallic activator ionic complex has a melt flow ratio ($I_{10}/I_2$) from 5 to 15, in which melt index 12 is measured according to ASTM D1238 (incorporated herein by reference in its entirety) at 190° C. and 2.16 kg load, and melt index $I_{10}$ is measured according to ASTM D1238 at 190° C. and 10 kg load. In other embodiments the melt flow ratio ($I_{10}/I_2$) is from 5 to 10, and in others, the melt flow ratio is from 5 to 9.

In some embodiments, the polymer resulting from the catalyst system that includes the metal-ligand complex and the bimetallic activator ionic complex has a molecular-weight distribution (MWD) from 1 to 25, where MWD is defined as Mw/Mn with Mw being a weight-average molecular weight and Mn being a number-average molecular weight. In other embodiments, the polymers resulting from the catalyst system have a MWD from 1 to 6. Another embodiment includes a MWD from 1 to 3; and other embodiments include MWD from 1.5 to 2.5.

Continuous Polymerization

Raw materials (ethylene, 1-octene) and the process solvent (a narrow boiling range high-purity isoparaffinic solvent trademarked ISOPAR E commercially available from ExxonMobil Corporation) are purified with molecular sieves before introduction into the reaction environment. Hydrogen is supplied in pressurized cylinders as a high purity grade and is not purified further. The reactor monomer feed (ethylene) stream is pressurized via mechanical compressor to above reaction pressure at 525 psig. The solvent and comonomer (1-octene) feed is pressurized via mechanical positive displacement pump to above reaction pressure at 525 psig. MMAO-3A, commercially available from Nouryon, is used as an impurity scavenger. The individual catalyst components (procatalyst/activator/scavenger) are manually batch diluted to specified component concentrations with purified solvent (Isopar E) and pressured to above reaction pressure at 525 psig. The activator is used at a 1.2 molar ratio relative to the procatalyst. The scavenger is used at a constant flow such that its contribution to the in-reactor Al concentration is 0.6 ppm. All reaction feed flows are measured with mass flow meters and independently controlled with computer automated valve control systems.

The continuous solution polymerizations are carried out in a 1 gallon continuously stirred-tank reactor (CSTR). The combined solvent, monomer, comonomer and hydrogen feed to the reactor is temperature controlled between 5° C. and 30° C. and is typically 15° C. All of these materials are fed to the polymerization reactor with the solvent feed. The catalyst is fed to the reactor to reach a specified conversion of ethylene. The activator is fed separately based on a calculated specified molar ratio (1.2 molar equivalents) to the catalyst component. The TEA scavenger shares the same line as the activator and flow is based on either an Al concentration in the reactor or a specified molar ratio to the catalyst component. The effluent from the polymerization reactor (containing solvent, monomer, comonomer, hydrogen, catalyst components, and molten polymer) exits the reactor and is contacted with water to terminate polymerization. In addition, various additives such as antioxidants can be added at this point. The stream then goes through a static mixer to evenly disperse the catalyst kill and additives.

Following additive addition, the effluent (containing solvent, monomer, comonomer, hydrogen, catalyst components, and molten polymer) passes through a heat exchanger to raise the stream temperature in preparation for separation of the polymer from the other lower-boiling reaction components. The stream then passes through the reactor pressure control valve, across which the pressure is greatly reduced. From there, it enters a two-stage separation system consisting of a devolatizer and a vacuum extruder, where solvent and unreacted hydrogen, monomer, comonomer, and water are removed from the polymer. At the exit of the extruder, the strand of molten polymer formed goes through a cold-water bath, where it solidifies. The strand is then fed through a strand chopper, where the polymer is cut into pellets after being air-dried.

Plaque Preparation for Electrical Testing

For all samples, the resin is added to a 420 mL Brabender mixer bowl with cam blades set at 80° C. and fluxed for 1 minute once melted. If the sample includes a partition agent, it is added to the resin and fluxed until the powder was visually incorporated. The antioxidant is added slowly, and the blend is fluxed for 3 minutes once melted. Perkadox BC-FF is melted in a sealed vial using a hot water bath set at 60° C. and the liquid peroxide is added and mix at 40 rpm for 3 minutes. The polymer melt temperature should not exceed 125° C. The mixture is removed from the mixing bowl and cold pressed into a 'pancake.'

For plaque preparation, the samples are first pressed at 120° C. for 3 minutes under low pressure (500 psi). Following the 3 minutes, the compression is switched to high pressure (2500 psi) at the same temperature for another 3 minutes. The samples are cut into even pieces and reloaded back into the press. Then the samples are pressed at 120° C. at low pressure for 3 minutes. Then, the temperature was raised to 182° C. and the pressure increased to high pressure conditions. Once the press reached the desired temperature, the samples are cured for further 12 minutes at high pressure. Following the cure time, samples are cooled to about 30° C. under high pressure.

A 50 mil and 20 mil plaque are made from the cold pressing using the plaque preparation and curing method above. The plaques are then placed in a vacuum oven and degassed for 3 days at 65° C. under house vacuum. Then sample discs are punched out to be tested for DC/DF (dielectric constant/dissipation factor) and VR (volume resistivity). Replicate samples are punched from the same plaque.

The dielectric constant and dissipation factor are measured using the ASTM D150-18 method; the volume resistivity (VR=Rxsample area x sample thickness$^{-1}$) is measured using the ASTM D257-14 method.

EXAMPLES

Examples 1-3 are synthetic procedures for intermediates of Activator 1 to Activator 3. In Example 4, various activators were used to synthesize polymer resins. The polymer resin characteristics were measured and recorded in Tables 1-3. One or more features of the present disclosure are illustrated in view of the examples as follows:

Example 1: Synthesis of Activator 1

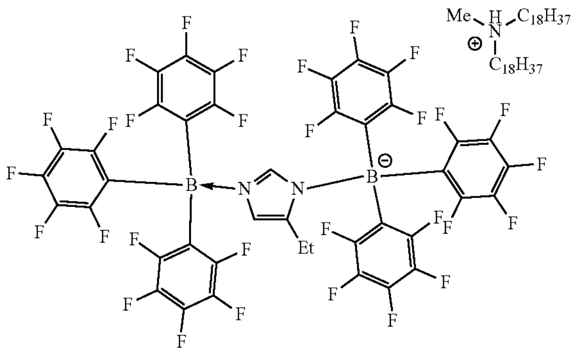

In a dry box, Armeen M2HT (3.35 g, 6.24 mmol), 4-ethylimidazole (0.600 g, 6.24 mmol), and tris(pentafluorophenyl)borane (6.39 g, 12.5 mmol) were transferred into a round-bottom flask and toluene (70 mL) was added. The reaction mixture was heated to 100° C. for 2 hours and then cooled to 25° C. The solvent was removed under vacuum. Pentane (50 mL) was added and the mixture was stirred vigorously for 30 minutes. The pentane was decanted and the remaining oil was further dried under vacuum yielding the product as a light brown oil (9.63 g, 93%). $^{1}$H NMR (400 MHz, Benzene-$d_6$) δ 7.97 (d, J=4.7 Hz, 1H), 6.90 (s, 1H), 1.98 (d, J=7.8 Hz, 4H), 1.73 (s, 3H), 1.46-1.24 (m, 57H), 0.91 (q, J=5.8, 4.8 Hz, 16H), 0.79 (t, J=7.4 Hz, 3H). $^{19}$F NMR (376 MHz, Benzene-$d_6$) δ: −128.35, −128.51--128.90, −130.74--131.38 (m), −132.14 (d, J=22.5 Hz), −133.56 (d, J=85.7 Hz), −135.62 (d, J=24.5 Hz), −138.96, −156.96 (t, J=20.8 Hz), −157.97, −158.47 (t, J=20.7 Hzz), −158.98, −161.46 (td, J=23.2, 22.7, 7.3 Hz), −164.19--164.97 (m), −165.16--166.34 (m).

Synthesis of 2-Bromodecanal

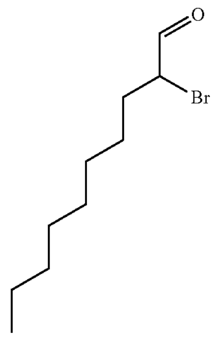

A round-bottom flask was charged with the 1-decanal (5.00 g, 32 mmol) and dissolved in 200 mL chloroform. The bromine (3.99 g, 25 mmol, 0.78 eq.) was dissolved in chloroform (200 mL) and loaded into an addition funnel. Using the addition funnel, the bromine solution was added dropwise into the decanal solution. After the addition was complete, the reaction was checked by GC/MS, confirming complete conversion to the desired product. The solution was slowly poured over 100 mL of a saturated sodium bicarbonate solution. The organic layer was separated, washed (3×80 mL) with water, dried over sodium sulfate, filtered, and the solvent removed by rotovap. Reagent was used as is in subsequent reactions (Yield: 7.52 g, 86%). $^{1}$H NMR (400 MHz, Chloroform-d) δ 9.42 (d, J=3.1 Hz, 1H), 4.21 (ddd, J=8.2, 6.2, 3.1 Hz, 1H), 2.03 (ddt, J=14.5, 9.9, 5.9 Hz, 1H), 1.90 (dddd, J=14.6, 9.9, 8.1, 5.1 Hz, 1H), 1.35-1.18 (m, 10H), 0.93-0.80 (m, 3H). $^{13}$C NMR (101 MHz, Chloroform-d) δ 192.74, 55.41, 31.72, 31.61, 29.18, 29.06, 28.85, 26.86, 22.57, 14.02.

Synthesis of 4-octyl-1H-imidazole

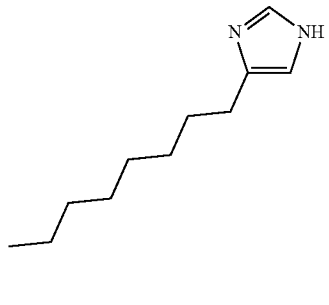

A round bottom flask was charged with 2-bromooctanal (4.3 g, 18.3 mmol), formamide (5.8, 146.3 mmol), and a stir-bar. The solution was heated to 185° C. with a reflux condenser and stirred overnight. The solution was cooled, an aliquot was taken, quenched with water, and analyzed by GC/MS to evaluate conversion. The solution was brought back up to 185° C. and refluxed overnight. After cooling to room temperature, the reaction solution separated into a dark viscous oily top layer and a light water-like bottom layer. Both were sampled with the bottom layer showing more product. The entire solution was quenched with ice water, then transferred to a separatory funnel. The aqueous solution was washed three times with $CH_2Cl_2$. The organic phase was dried over sodium sulfate overnight. An aliquot of the solution was taken and the solvent removed under vacuum. The brown oil was then purified by silica-gel column chromatography (Yield: 410 mg, 12%). $^1$H NMR (400 MHz, Chloroform-d) δ 12.49 (s, 1H), 7.52 (s, 1H), 6.73 (s, 1H), 2.57 (t, J=7.7 Hz, 1H), 1.60 (p, J=7.5 Hz, 1H), 1.48-0.99 (m, 12H), 0.83 (q, J=4.0, 2.9 Hz, 3H). $^{13}$C NMR (101 MHz, Chloroform-d) δ 136.67, 134.31, 117.95, 31.91, 29.51, 29.46, 29.40, 29.31, 26.62, 22.69, 14.11.

Example 2: Synthesis of Activator 2

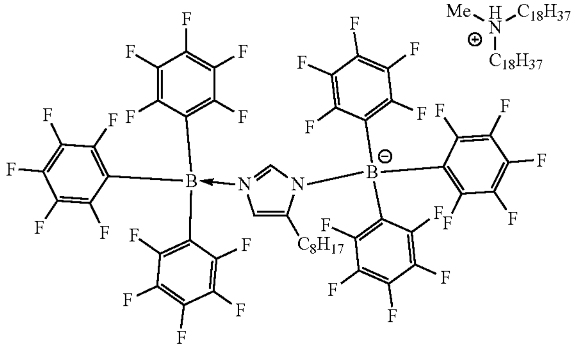

In a dry box, the solids Armeen M2HT (907 mg, 1.69 mmol), 4-octyl-imidazole (305 mg, 1.69 mmol), tris(pentafluorophenyl)borate (FAB, 1.73 g, 3.38 mmol), and toluene (5 mL) were each charged into a flask. The reaction was heated to 100° C., during which it became homogeneous. After 2 hrs, the reaction was analyzed by $^{19}$F NMR analysis, confirming complete conversion was not definitive, but there was no FAB present in the F19 ($C_6D_6$) spectra. The toluene was mostly removed in vacuo, then 40 mL pentane were added and the mixture stirred vigorously for at least 30 minutes. The stirring was stopped, chilled to 0° C., and the solution allowed to phase separate. Most of the pentane solution was decanted off, then the remaining oil and solvent trace were dried in vacuo, resulting in 1.95 g of a viscous red-brown oil. The decanted pentane was moved back to the refrigerator to see if additional material would oil out. No appreciable separation occurred after several days at 0° C. The solvent was removed in vacuo (Yield: ~1 g, 34%). $^1$H NMR (400 MHz, Benzene-$d_6$) δ 7.97 (d, J=4.8 Hz, 1H), 6.92 (s, 1H), 3.04 (s, 1H), 2.65 (s, 1H), 1.89 (s, 3H), 1.70 (s, 3H), 1.46-1.23 (m, 47H), 1.23-1.08 (m, 3H), 1.04 (q, J=7.1 Hz, 7H), 0.90 (dt, J=14.7, 7.0 Hz, 9H), 0.85-0.68 (m, 9H). $^{19}$F NMR (376 MHz, Benzene-$d_6$, 23° C.) δ −128.02 (1F), −128.88 (1F), −130.82 (1F, d, J=23.5 Hz), −132.14 (6F, d, J=22.5 Hz), −133.54 (1F), −134.23 (1F), −138.37 (1F), −156.88 (1F, t, J=21.0 Hz), −157.93 (1F), −158.33 (6F, t, J=20.8 Hz), −158.92 (1F), −160.83--161.59 (1F, m), −164.15, −164.42 (6F, t, J=20.6 Hz), −165.48 (1F), −165.98 (1F). $^{19}$F NMR (376 MHz, Toluene-$d_8$, 80° C.) δ −128.02, −131.00, −131.83 (d, J=21.5 Hz), −133.48, −158.02, −159.21 (t, J=20.0 Hz), −164.63--165.12 (m), −165.63.

Synthesis of 5-((dimethyl(octyl)silyl)methyl)benzo[c][1,2,5]thiadiazole

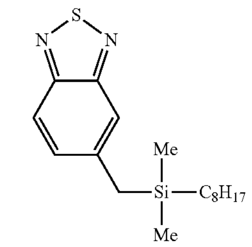

In a nitrogen-filled glovebox, a reaction vial was charged with a 0.88 M solution of ((dimethyl(octyl)silyl)methyl) magnesium chloride in diethyl ether (1.36 mL, 1.20 mmol, 1.2 equiv.). A solution of zinc chloride (245 mg, 1.8 equiv.) in THF (2.5 mL) was added dropwise, resulting in the immediate precipitation of a white solid. The suspension was stirred at room temperature for 1 h. 5-bromobenzo[c][1,2,5]thiadiazole (215 mg, 1.00 mmol, 1 equiv.) and CPhos G3 precatalyst (8.1 mg, 0.01 mmol, 1 mol %) were added, and the reaction mixture was stirred at room temperature for 18 h. The mixture was removed from the glovebox. The reaction mixture was passed through a plug of silica gel, and the plug was eluted with dichloromethane (2×20 mL) to afford an amber solution. The solution was concentrated in vacuo. The material was adsorbed onto silica gel and purified by flash column chromatography (40 g, 0.1-2% EtOAc in hexane) to afford the product as a clear oil (286.2 mg, 89% yield). $^1$H NMR (400 MHz, Chloroform-d) δ 7.83 (dd, J=9.0, 0.7 Hz, 1H), 7.58-7.51 (m, 1H), 7.26 (dd, J=9.0, 1.7 Hz, 1H), 2.27 (s, 2H), 1.38-1.18 (m, 12H), 0.88 (t, J=6.8 Hz, 3H), 0.55 (dd, J=9.6, 5.9 Hz, 2H), 0.01 (s, 6H). $^{13}$C NMR (101 MHz, Chloroform-d) δ 155.55, 153.02, 143.24, 132.51, 120.39, 117.56, 33.55, 31.91, 29.29, 29.22, 26.56, 23.71, 22.66, 14.79, 14.11, −3.49.

Synthesis of 4-((dimethyl(octyl)silyl)methyl)benzene-1,2-diamine

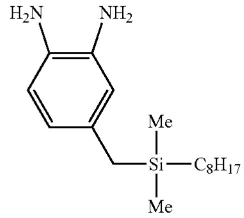

In a nitrogen-filled glovebox, 5-((dimethyl(octyl)silyl)methyl)benzo[c][1,2,5]thiadiazole (0.2862 g, 0.893 mmol, 1 equiv.) was dissolved in tetrahydrofuran (30 mL). Lithium aluminum hydride (135.5 mg, 3.57 mg, 4 equiv.) was added portion wise over several minutes. The lithium aluminum hydride vial was rinsed with THF (2×5 mL), and the rinses were added to the reaction mixture. The clear, colorless solution became pink during the addition. The reaction was stirred at room temperature for 2.5 h, during which time the solution became clear and colorless. The reaction vessel was sealed with a septum, removed from the glovebox, and cooled to 0° C. in an ice bath. The solution was subjected to a Fieser workup. Water (0.14 mL), 15% aqueous NaOH (0.14 mL), and water (0.42 mL) were sequentially added dropwise via syringe. The ice bath was removed and the reaction mixture was stirred at room temperature for 15 min, resulting in a light pink solution. Anhydrous magnesium sulfate was added, and the reaction mixture was stirred for an additional 10 min. The solution was filtered and concentrated in vacuo to afford the product as a white solid (250.6 mg, 96% yield). $^1$H NMR (400 MHz, Chloroform-d) δ 6.60 (d, J=7.5 Hz, 1H), 6.37 (d, J=9.3 Hz, 2H), 3.30 (s, 4H), 1.95 (s, 2H), 1.30 (s, 12H), 0.92 (td, J=7.1, 5.9, 3.4 Hz, 3H), 0.57-0.43 (m, 2H), −0.03 (t, J=2.1 Hz, 6H). $^{13}$C NMR (101 MHz, Chloroform-d) δ 135.07, 132.59, 130.53, 119.69, 117.31, 116.50, 33.68, 31.98, 29.37, 29.30, 24.51, 23.83, 22.71, 14.87, 14.15, −3.48. HRMS (ESI) Calculated for $C_{17}H_{32}N_2Si$ [M+1]: 293.2408; found 293.2403.

Synthesis of 6-((dimethyl(octyl)silyl)methyl)-1H-benzo[d]imidazole

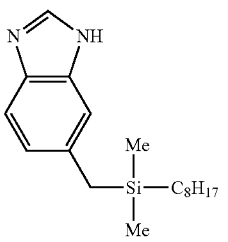

A round bottom flask was charged with 4-((dimethyl (octyl)silyl)methyl)benzene-1,2-diamine (250.6 mg, 0.857 mmol, 1 equiv.), triethylorthoformate (0.17 mL, 1.03 mmol, 1.2 equiv.), acetonitrile (3 mL), and dichloromethane (3 mL). Iodine (21.7 mg, 0.0806 mmol, 10 mol %) was added, and the reaction was stirred at room temperature for 7 h. The solution turned from brown to dark green, then back to brown again. The solution was concentrated in vacuo to afford a brown oil. The material was adsorbed onto Celite, then purified by flash column chromatography. The silica gel column cartridge was first flushed with 60 mL of 10% triethylamine in hexane. Next, the column was equilibrated with 0.1% MeOH in dichloromethane, and a typical flash column chromatography run was performed (24 g silica gel, 0.1-7% MeOH in dichloromethane) to afford a brown oil (191.1 mg, 74% yield). $^1$H NMR (400 MHz, Chloroform-d) δ 12.31-11.89 (m, 1H), 8.14 (d, J=2.8 Hz, 1H), 7.58 (dd, J=8.3, 1.3 Hz, 1H), 7.32 (s, 1H), 6.99 (dd, J=8.4, 1.5 Hz, 1H), 2.23 (s, 2H), 1.29 (d, J=15.7 Hz, 12H), 0.90 (t, J=6.8 Hz, 3H), 0.55 (dd, J=9.6, 5.7 Hz, 2H), −0.01 (s, 6H). $^{13}$C NMR (101 MHz, Chloroform-d) δ 140.13, 137.40, 135.64, 135.59, 123.90, 115.42, 113.26, 33.66, 31.95, 29.36, 29.27, 25.69, 23.82, 22.69, 14.87, 14.14, −3.51. HRMS (ESI) Calculated for $C_{18}H_{30}N_2Si$ [M+1]: 303.2251; found 303.2242.

Example 3: Synthesis of Activator 3

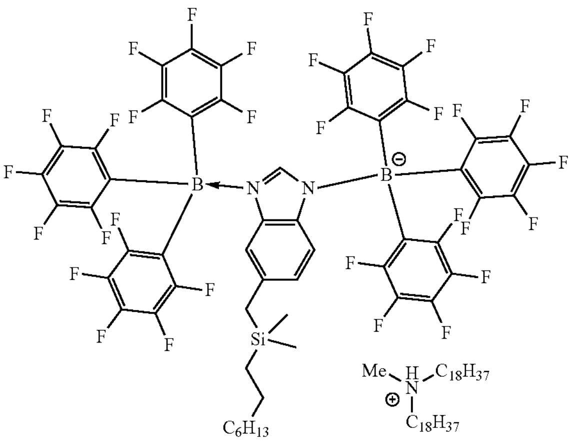

In a nitrogen-filled glovebox, a reaction vial was charged with 6-((dimethyl(octyl)silyl)methyl)-1H-benzo[d]imidazole (35.4 mg, 0.117 mmol, 1 equiv.), tris(pentafluorophenyl)borane (119.8 mg, 0.234 mmol, 2 equiv.), Armeen M2HT (62.7 mg, 0.117 mmol, 1 equiv.), and toluene (2 mL). The reaction was stirred at 100° C. for 18 h. The solution was passed through a 0.45 μm syringe filter in line with a 0.2 μm syringe filter. The filters were washed with toluene (2×0.5 mL). The combined filtrates were concentrated in vacuo to afford an amber oil. The oil was triturated with hexane (5 mL). The material was concentrated in vacuo, yielding a light yellow solid. The solid was triturated with hexane (5 mL). All volatiles were removed in vacuo to afford a yellow solid (207.1 mg, 95% yield). $^1$H NMR (500 MHz, Toluene-$d_8$) δ 8.39 (s, 1H), 7.56 (d, J=8.5 Hz, 1H), 7.37 (s, 1H), 6.72 (d, J=8.6 Hz, 1H), 2.15-2.04 (m, 4H), 1.95 (d, J=13.1 Hz, 2H), 1.84 (s, 3H), 1.46-0.79 (m, 85H), 0.45-0.31 (m, 2H), −0.18 (s, 6H). $^{11}$B NMR (160 MHz, Toluene-$d_8$) δ −8.66 (br). $^{19}$F NMR (470 MHz, Toluene-$d_8$, 25° C.) δ −127.08--128.89 (m), −129.34, −130.41, −131.60--133.29 (m), −133.51--134.86 (m), −135.58 (d, J=24.3 Hz), −135.66--137.13 (m), −157.13, −157.85--159.33 (m), −159.76 (t, J=20.5 Hz), −161.19--162.04 (m), −163.73--164.30 (m), −164.47--164.83 (m), −165.06--165.93 (m). $^{19}$F NMR (470 MHz, Toluene-$d_8$, 90° C.) δ −132.15 (br s), −158.82 (br s), −165.28 (br s). HRMS (ESI) Calculated for $C_{37}H_{78}N$ [M+1]: 536.6129; found 536.6117. Calculated for $C_{54}H_{29}B_2F_{30}N_2Si$ [M-]: 1325.1813; found 1325.1810.

Example 4—Polymerization Results

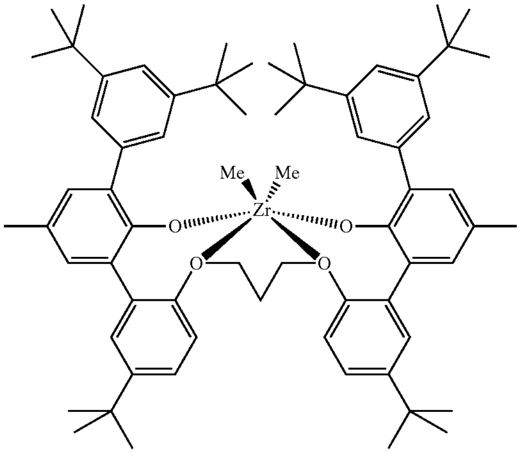

Procatalyst A

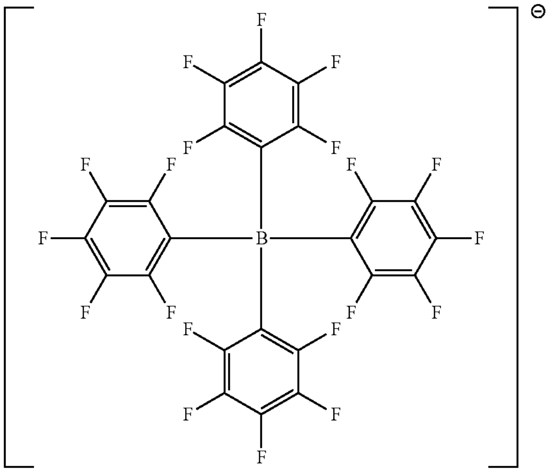

Comparative Activator C1

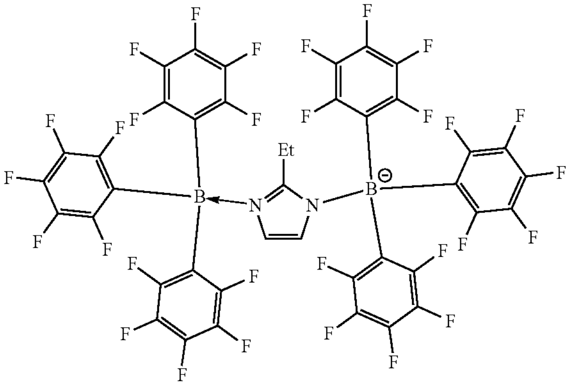

Comparative Activator C2

-continued

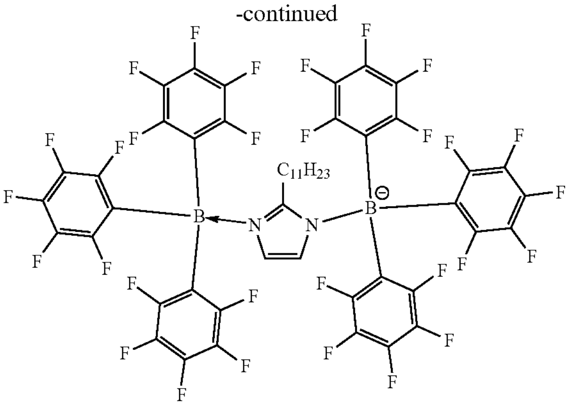

Comparative Activator C3

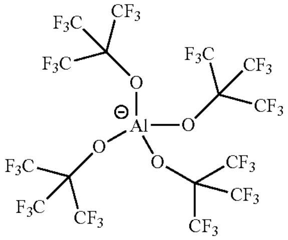

Comparative C4

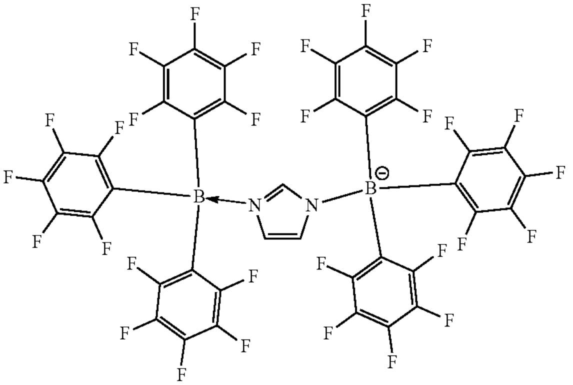

Comparative C5

The polymerizations were carried out in the Continuous Stir-Tank Reactor. The procedure is described in the Continuous Reactor section.

Each of the bimetallic Activators 1, 2, and 3, and a comparative activator C1 (herein “Comparative C1”) were mixed with Procatalyst A to form four catalyst systems. Comparative C1, Comparative C2, Comparative C3, Comparative C4, and Comparative C5 are compounds having $^{+}N(H)(Me)(C_{18}H_{37})_2$ as a countercation. Comparative C1 has been successfully used as an activator in industrial-scale olefin polymerization reactions.

While expanded borates have previously been reported as competent activators in U.S. Pat. No. 6,395,671B2, unsubstituted imidazole-based borates like Comparative C5 do not have low solubility in aliphatic hydrocarbon solvents preventing their use in systems that either cannot tolerate aromatic residuals or where a more complex slurry-based delivery system is not applicable.

TABLE 1

Reactor Conditions for Polymerization reaction conducted in the CSTR reactor.

| Activator | Temp (° C.) | Solvent (lb/h) | C2 Feed (lb/h) | C8 Feed (lb/h) | Conversion (%) | Production rate (lb/h) | Exit $C_2$ (lb/h) | Exit $C_8$ (lb/h) |
|---|---|---|---|---|---|---|---|---|
| Comparative C1 | 170 | 35.9 | 4.21 | 8.93 | 76.9 | 5.15 | 0.971 | 7.01 |
| Comparative C2 | 170 | 35.9 | 4.2 | 8.54 | 76.6 | 5.18 | 0.982 | 6.57 |
| Comparative C3 | 170 | 35.9 | 4.2 | 8.54 | 77 | 5.28 | 0.968 | 6.49 |
| Comparative C4 | 170 | 36.5 | 4.21 | 9.36 | 76.2 | 5.27 | 1 | 7.29 |
| Activator 1 | 170 | 36.5 | 4.2 | 8.62 | 77.7 | 5.02 | 0.939 | 6.86 |
| Activator 2 | 170 | 35.9 | 4.21 | 8.54 | 76.6 | 5.23 | 0.982 | 6.53 |
| Activator 3 | 170 | 35.7 | 4.2 | 8.53 | 75 | 5.01 | 1.05 | 6.68 |

The efficiencies of the inventive Activators 1, 2, and 3, and Comparative $C_1$-$C_3$ and the polymer characteristics of the polymers yielded from the inventive Activators 1, 2, and 3, and Comparative C1 were determined. The results are summarized in Table 1. The Comparative C1 has been successfully used in industrial applications.

TABLE 2

Absolute Efficiency and Relative Efficiency for Procatalyst A and Activators 1-3

| Activator | Efficiency[a] (MM) | Comparative C4 Efficiency (MM) | Relative Efficiency[b] |
|---|---|---|---|
| Activator 1 | 2.90 | 3.1 | 0.93 |
| Activator 2 | 1.26 | 1.0 | 1.26 |
| Comparative C2 | 0.08 | 0.85 | 0.09 |
| Comparative C3 | 0.07 | 0.85 | 0.08 |
| Activator 3 | 0.10 | 0.8 | 0.12 |
| Comparative C1 | 4.55 | | |

[a]Efficiency is grams of polymer per grams of metal (g of poly/g of metal).

[b]Relative Efficiency was calculated for each activator based on the efficiency of Comparative C4 obtained under identical reaction conditions.

TABLE 3

Polymer Properties of Resins Produced with Procatalyst A and Activators

| Activator | $I_2$ | $M_n$ | $M_w$ | $M_w/M_n$ | Dens. (g/cm$^3$) | $T_c$ | $T_m$ |
|---|---|---|---|---|---|---|---|
| Comparative C1 | 5.19 | 36,265 | 73,840 | 2.04 | 0.875 | 50.5 | 68 |
| Comparative C2 | 5.36 | 37,149 | 74,561 | 2.01 | 0.874 | 48.9 | 65.2 |
| Comparative C3 | 5.90 | 36,263 | 73,075 | 2.02 | 0.873 | 48.1 | 65.3 |
| Comparative C4 | 5.74 | 33,914 | 68,982 | 2.03 | 0.876 | 50.9 | 68.8 |
| Activator 1 | 4.61 | 37,358 | 75,856 | 2.03 | 0.874 | 49.5 | 67.1 |
| Activator 2 | 5.27 | 37,045 | 74,905 | 2.02 | 0.874 | 49.6 | 66.3 |

TABLE 4

Solubility of activators in hydrocarbon solvents

| Activator | Solvent | Solubility at room temperature (wt %) |
|---|---|---|
| Comparative C5 | Methylcyclohexane | <0.1 |
| Activator 1 | Methylcyclohexane | 1 |
| Activator 2 | Methylcyclohexane | 2 |
| Activator 3 | Methylcyclohexane | 0.5 |

Substitution of the central imidazole component at the R1 position (as shown in activators Comparative C2 and C3) resulted in an increase in the activator's solubility in aliphatic hydrocarbons. However, it is believe that the substitution in the $R^1$ position affected the efficacy of the activators (as tabulated in Table 2).

Comparatively, a substitution at the $R^3$ or R2 positions on the imidazole (as shown in Activators 1, 2, and 3) increased the solubility of the activator in aliphatic hydrocarbons when compared to Comparative C5, while providing improved catalyst efficiency when compared to substitution at the $R^1$ position (C2 and C3).

TABLE 5

Conductivity results of plaques made using Procatalyst A and activators.

| Activator | Conductivity (aS/cm) |
|---|---|
| Comparative C1 | >8000 |
| Activator 1 | 1537 |
| Activator 2 | 1909 |

Activator 1 and Activator 2, when in a catalyst system that included Procatalyst A, produced polymers with a substantial decrease in conductivity than when compared to the polymer produced by Procatalyst A and the activator Comparative C1.

Equipment Standards

All solvents and reagents are obtained from commercial sources and used as received unless otherwise noted. Anhydrous toluene, hexanes, tetrahydrofuran, and diethyl ether are purified via passage through activated alumina and, in some cases, Q-5 reactant. Solvents used for experiments performed in a nitrogen-filled glovebox are further dried by storage over activated 4A molecular sieves. Glassware for moisture-sensitive reactions is dried in an oven overnight prior to use. NMR spectra are recorded on Varian 400-MR and VNMRS-500 spectrometers. LC-MS analyses are performed using a Waters e2695 Separations Module coupled with a Waters 2424 ELS detector, a Waters 2998 PDA detector, and a Waters 3100 ESI mass detector. LC-MS separations are performed on an XBridge C18 3.5 μm 2.1×50 mm column using a 5:95 to 100:0 acetonitrile to water gradient with 0.1% formic acid as the ionizing agent. HRMS analyses are performed using an Agilent 1290 Infinity LC with a Zorbax Eclipse Plus C18 1.8 μm 2.1×50 mm column coupled with an Agilent 6230 TOF Mass Spectrometer with electrospray ionization. $^1$H NMR data are reported as follows: chemical shift (multiplicity (br=broad, s=singlet, d=doublet, t=triplet, q=quartet, p=pentet, sex=sextet, sept=septet and m=multiplet), integration, and assignment). Chemical shifts for $^1$H NMR data are reported in ppm downfield from internal tetramethylsilane (TMS, 8 scale) using residual protons in the deuterated solvent as references. $^{13}C$ NMR data are determined with $^{1}H$ decoupling, and the chemical shifts are reported downfield from tetramethylsilane (TMS, 8 scale) in ppm versus the using residual carbons in the deuterated solvent as references. Dielectric Constant and Dissipation Factor are measured using a Haefely 2830/2831 Precision Dielectric Analyzer and a Haefely 2914 Solid Test Cell. Volume resistivity is measured using a Keithley 6517B Electrometer and a Keithley 8009 Resistivity Test Fixture.

The invention claimed is:

1. A process of polymerizing olefins, the process comprising contacting ethylene and a $(C_3\text{-}C_{40})$alpha-olefin comonomer in the presence of a catalyst system comprising a procatalyst and a bimetallic activator complex, the bimetallic activator complex comprising an anion and a countercation, the anion having a structure according to formula (I):

(I)

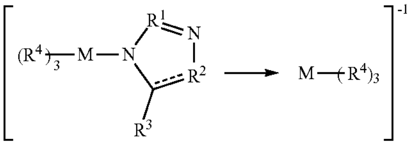

where:

each M is independently aluminum or boron;

$R^1$ is C(H);

$R^2$ is selected from $C(R^L)$ or N, wherein each $R^L$ is independently —H or a bond connected to $R^3$;

$R^3$ is chosen from $(C_1\text{-}C_{30})$hydrocarbyl, $(C_1\text{-}C_{30})$heterohydrocarbyl, or $(C_2\text{-}C_{30})$hydrocarbylene connected to $R^2$;

each $R^4$ is independently selected from the group consisting of a halogen-substituted $(C_1\text{-}C_{30})$alkyl substituted with at least three fluorine atoms, and radicals having formula (II):

(II)

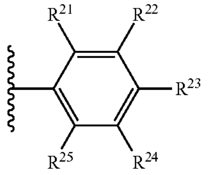

in which $R^{21}$, $R^{22}$, $R^{23}$, $R^{24}$, and $R^{25}$ are independently chosen from halogen-substituted $(C_1\text{-}C_{40})$alkyl, halogen-substituted $(C_6\text{-}C_{40})$aryl, —H, $—NR^N_2$, $—OR^C$, $—SR^C$, or halogen, provided that at least three of $R^{21\text{-}25}$ are selected from the group consisting of halogen-substituted $(C_1\text{-}C_{40})$alkyl, halogen-substituted $(C_6\text{-}C_{40})$aryl, and —F;

each $R^N$ and each $R^C$ is independently $(C_1\text{-}C_{30})$hydrocarbyl or —H; and wherein one of:

$R^2$ is C(H); and $R^3$ is $(C_1\text{-}C_{10})$alkyl; or $R^3$ is connected to $R^2$ to form a ring, wherein the anion of the bimetallic activator complex has a structure according to formula (Ta):

(Ia)

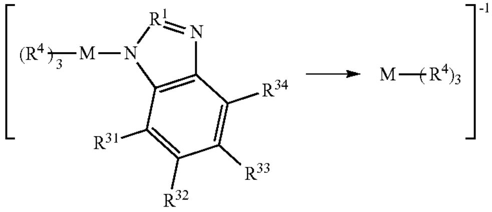

where $R^{31}$, $R^{32}$, $R^{33}$, and $R^{34}$ are independently a $(C_1\text{-}C_{30})$hydrocarbyl, $(C_1\text{-}C_{30})$heterohydrocarbyl, or —H; and $R^1$, $R^4$, and M are as defined in formula (I), and wherein at least one of $R^{32}$ and $R^{33}$ is $—CH_2Si(R^C)_3$, where each $R^C$ is independently $(C_1\text{-}C_{10})$alkyl.

2. The catalyst system according to claim 1, wherein each $R^4$ is $—C_6F_5$.

3. The catalyst system according to claim 1, wherein each M is boron.

4. The catalyst system according to claim 1, wherein $R^2$ is C(H).

5. The catalyst system according to claim 1, wherein $R^2$ is C(H); and $R^3$ is $(C_1\text{-}C_{10})$alkyl.

6. The catalyst system according to claim 1, wherein $R^2$ is C(H); and $R^3$ is methyl, ethyl, propyl, 2-propyl, n-butyl, tert-butyl, 2-methylpropyl, pentyl, hexyl, heptyl, n-octyl, or tert-octyl.

7. The catalyst system according to claim 1, wherein $R^2$ is C(H); and $R^3$ is n-octyl or tert-octyl.

8. The catalyst system according to claim 1, to $R^2$ wherein the anion of the bimetallic activator complex has a structure according to formula (Ia), where $R^{31}$, $R^{32}$, $R^{33}$, and $R^{34}$ are independently a $(C_1\text{-}C_{30})$hydrocarbyl, $(C_1\text{-}C_{30})$heterohydrocarbyl, or —H; and $R^1$, $R^4$, and M are as defined in formula (I), and wherein at least one of $R^{32}$ and $R^{33}$ is $—CH_2Si(R^C)_3$, where each $R^C$ is independently $(C_1\text{-}C_{10})$alkyl.

9. The catalyst system according to claim 8, wherein each $R^4$ is $—C_6F_5$.

10. The catalyst system according to claim 8, wherein at least one of $R^{32}$ and $R^{33}$ is $—CH_2Si(CH_3)_2(R^C)$, where $R^C$ is independently $(C_1\text{-}C_{10})$alkyl.

11. The catalyst system according to claim 8, wherein at least one of $R^{32}$ and $R^{33}$ is $—CH_2Si(CH_3)_2(C_8H_{17})$.

* * * * *